US012347568B2

(12) United States Patent
Balaban et al.

(10) Patent No.: US 12,347,568 B2
(45) Date of Patent: *Jul. 1, 2025

(54) PHYSIOLOGICAL RESPONSE PREDICTION SYSTEM

(71) Applicant: Intermountain Intellectual Asset Management, LLC, Salt Lake City, UT (US)

(72) Inventors: David John Balaban, San Diego, CA (US); Mark Joseph Durst, San Diego, CA (US); Todd W. Kelley, San Diego, CA (US); John Scott Skellenger, San Diego, CA (US); Mikhail Toupikov, San Diego, CA (US); Nicolas Sean Frisby, San Diego, CA (US); Dominic Joseph Steinitz, San Diego, CA (US)

(73) Assignee: Intermountain Intellectual Asset Management, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/352,954

(22) Filed: Jul. 14, 2023

(65) Prior Publication Data

US 2024/0047076 A1   Feb. 8, 2024

Related U.S. Application Data

(63) Continuation of application No. 16/527,819, filed on Jul. 31, 2019, now Pat. No. 11,749,411, which is a
(Continued)

(51) Int. Cl.
*G16H 50/50* (2018.01)
*G06N 7/01* (2023.01)
(Continued)

(52) U.S. Cl.
CPC ............. *G16H 50/50* (2018.01); *G06N 7/01* (2023.01); *G16B 5/20* (2019.02); *G16H 50/20* (2018.01)

(58) Field of Classification Search
None
See application file for complete search history.

(56) References Cited

U.S. PATENT DOCUMENTS 6,937,257 B1 *  8/2005  Dunlavey .............. G16B 45/00
                                                  715/764
7,319,945 B1    1/2008  Shapiro et al.
(Continued)

FOREIGN PATENT DOCUMENTS

CN          105550484 A      5/2016

OTHER PUBLICATIONS

Advisory Action dated Jul. 8, 2020 issued in U.S. Appl. No. 16/297,482.
(Continued)

*Primary Examiner* — Sultana M Zalalee
(74) *Attorney, Agent, or Firm* — Dorsey & Whitney LLP

(57) ABSTRACT

A system for modeling the evolution of a system overtime using an advection-based process is provided. The system continuously evolves a probability density function ("PDF") for a characteristic of a characteristic of the state of the system and its time-varying parameters. The PDF is evolved based on advection by solving an advection partial differential equation that is based on a system model of the system. The system model has time-varying parameters for modeling the characteristic of the state of the system. The system uses the continuously evolving PDF to make predictions about the characteristic of the state of the system.

9 Claims, 14 Drawing Sheets

Related U.S. Application Data continuation-in-part of application No. 16/297,482, filed on Mar. 8, 2019, now abandoned.

(60) Provisional application No. 62/839,467, filed on Apr. 26, 2019, provisional application No. 62/783,127, filed on Dec. 20, 2018, provisional application No. 62/739,016, filed on Sep. 28, 2018, provisional application No. 62/733,988, filed on Sep. 20, 2018, provisional application No. 62/720,084, filed on Aug. 20, 2018.

(51) Int. Cl.
*G16B 5/20* (2019.01)
*G16H 50/20* (2018.01)

(56) References Cited

U.S. PATENT DOCUMENTS

| | | | |
|---|---|---|---|
| 8,542,898 | B2 | 9/2013 | Bathe et al. |
| 9,141,756 | B1 | 9/2015 | Hillis et al. |
| 2001/0047252 | A1 | 11/2001 | Brown |
| 2003/0009099 | A1* | 1/2003 | Lett .................. G05B 17/02 600/416 |
| 2003/0144798 | A1 | 7/2003 | Gardner |
| 2003/0207338 | A1 | 11/2003 | Sklar et al. |
| 2004/0039530 | A1 | 2/2004 | Leesman et al. |
| 2005/0143927 | A1 | 6/2005 | Cammia et al. |
| 2005/0187747 | A1* | 8/2005 | Paxson ................. G16B 5/00 703/11 |
| 2009/0104653 | A1 | 4/2009 | Paldus et al. |
| 2010/0002925 | A1 | 1/2010 | Kiraly et al. |
| 2010/0049492 | A1* | 2/2010 | Bajaria ............. G01N 33/5082 703/11 |
| 2010/0285082 | A1 | 11/2010 | Fernandez |
| 2011/0046887 | A1 | 2/2011 | Veldhuis et al. |
| 2011/0131312 | A1 | 6/2011 | Marrow et al. |
| 2013/0179078 | A1 | 7/2013 | Griffon |
| 2015/0202440 | A1 | 7/2015 | Moehlis et al. |
| 2017/0150928 | A1 | 6/2017 | Del Alamo De Pedro et al. |
| 2017/0367617 | A1 | 12/2017 | Albanese et al. |
| 2018/0060758 | A1 | 3/2018 | Alexandrov et al. |
| 2018/0330062 | A1 | 11/2018 | Balaban et al. |
| 2020/0224172 | A1 | 7/2020 | Schiebinger et al. |

OTHER PUBLICATIONS

Eisen, Martin M. "Mathematical models in cell biology and cancer chemotherapy" (1979) (pp. 73-75, 81-82, 86-87, 172-176).

Final Office Action dated Feb. 21, 2020 issued in U.S. Appl. No. 16/297,482.

https://web.archive.org/web/20181230190500/https://en.wikipedia.org/wiki/advection (Year: 2018).

International Search Report and Written Opinion dated Jan. 21, 2020 received in international patent application No. PCT/US2019/044384.

Khalil, M., H., et al., "A review of Current Studies on Complexity of Algorithms for Partial Differential Equations," Department of Statistics & Computer Science, University of Delaware, Oct. 1976.

Luttinen, J., et al., "Linear State-Space Model with Time-Varying Dynamics," Aalto University, Finland, Oct. 2014.

Non-Final Office Action dated Nov. 8, 2022 issued in U.S. Appl. No. 16/527,819.

Non-Final Office Action dated Oct. 30, 2019 issued in U.S. Appl. No. 16/297,482.

Non-Final Office Action dated Sep. 28, 2020 issued in U.S. Appl. No. 16/297,482.

Tartakovsky, M., D., et al., "Probability destiny functions for advective-reactive transport with uncertain reaction rates," Water Resources Research, vol. 45, W07414, doi: 10.1029/2008WR007383, 2009.

* cited by examiner

PHYSIOLOGICAL RESPONSE PREDICTION SYSTEM

CROSS REFERENCE TO RELATED APPLICATIONS

This application is a continuation of U.S. patent application Ser. No. 16/527,819, filed Jul. 31, 2019, entitled "PHYSIOLOGICAL RESPONSE PREDICTION SYSTEM," which claims the benefit of priority of U.S. Provisional Application No. 62/839,467, filed Apr. 26, 2019, entitled "COMPILATION OF NAVICAN MODELING COMPONENTS;" U.S. patent application Ser. No. 16/527,819 is also a continuation-in-part of U.S. patent application Ser. No. 16/297,482, filed Mar. 8, 2019, entitled "PREDICTING STATE OF A SYSTEM BASED ON ADVECTION," which claims benefit of priority of U.S. Provisional Application No. 62/783,127, filed Dec. 20, 2018, entitled "ADDITIONAL COMPONENT MODELS," U.S. Provisional Application No. 62/739,016, filed Sep. 28, 2018, entitled "MODELING RESISTANCE TO CANCER TREATMENT," U.S. Provisional Application No. 62/733,988, filed Sep. 20, 2018, entitled "COMPONENT-BASED MECHANISTIC MODELS FOR BAYESIAN LEARNING," and U.S. Provisional Application No. 62/720,084, filed Aug. 20, 2018, entitled "PREDICTION BEHAVIOR OF BIOLOGICAL SYSTEM," which are all incorporated by reference herein in their entireties.

BACKGROUND

Current techniques for deciding on a medical treatment for a patient often rely on expected efficacy and adverse effects for a population of cohorts (which may be a very large population) or for even a general population. The actual efficacy and adverse effects on an individual patient, however, may be very different from those that are expected for such a population. For example, it is well-known that acetaminophen has an adverse effect on the liver, which is the death of hepatocytes (i.e., liver cells). Acetaminophen can be used as a medical treatment, for example, to relieve pain in a patient with cancer. The expected adverse effect for a population may depend on an expected death rate of liver cells. The actual death rate of liver cells, however, can vary significantly among patients. As a result, a patient with a low death rate of liver cells may not be treated with acetaminophen even though the adverse effects would be minimal. Conversely, a patient with a high death rate of liver cell may be treated with acetaminophen even though the adverse effects will be significant.

The ability to accurately predict the physiological response of an individual patient to medical treatment has the potential to significantly improve patient outcome. With a more accurate prediction of physiological response, the efficacy and any adverse effects of a medical treatment can also be more accurately predicted. A medical provider can then determine whether to proceed with the medical treatment based on the predicted efficacy and adverse effects. In addition, if the physiological response of the patent can be accurately predicted for different candidate medical treatments (e.g., different dosages of a drug or different drugs), a medical provider can balance the efficacy and adverse effects of those candidate medical treatments to select the most appropriate medical treatment for a patient. Continuing with the acetaminophen example, if the resulting adverse effects on the liver of that patient can be accurately predicted, a medical provider can decide whether to proceed with an acetaminophen as a medical treatment and, if so, with what dosage. Thus, the ability to provide more personalized and thus more effective medical treatment can significantly improve medical treatment for most patients.

DETAILED DESCRIPTION

Figure 1:
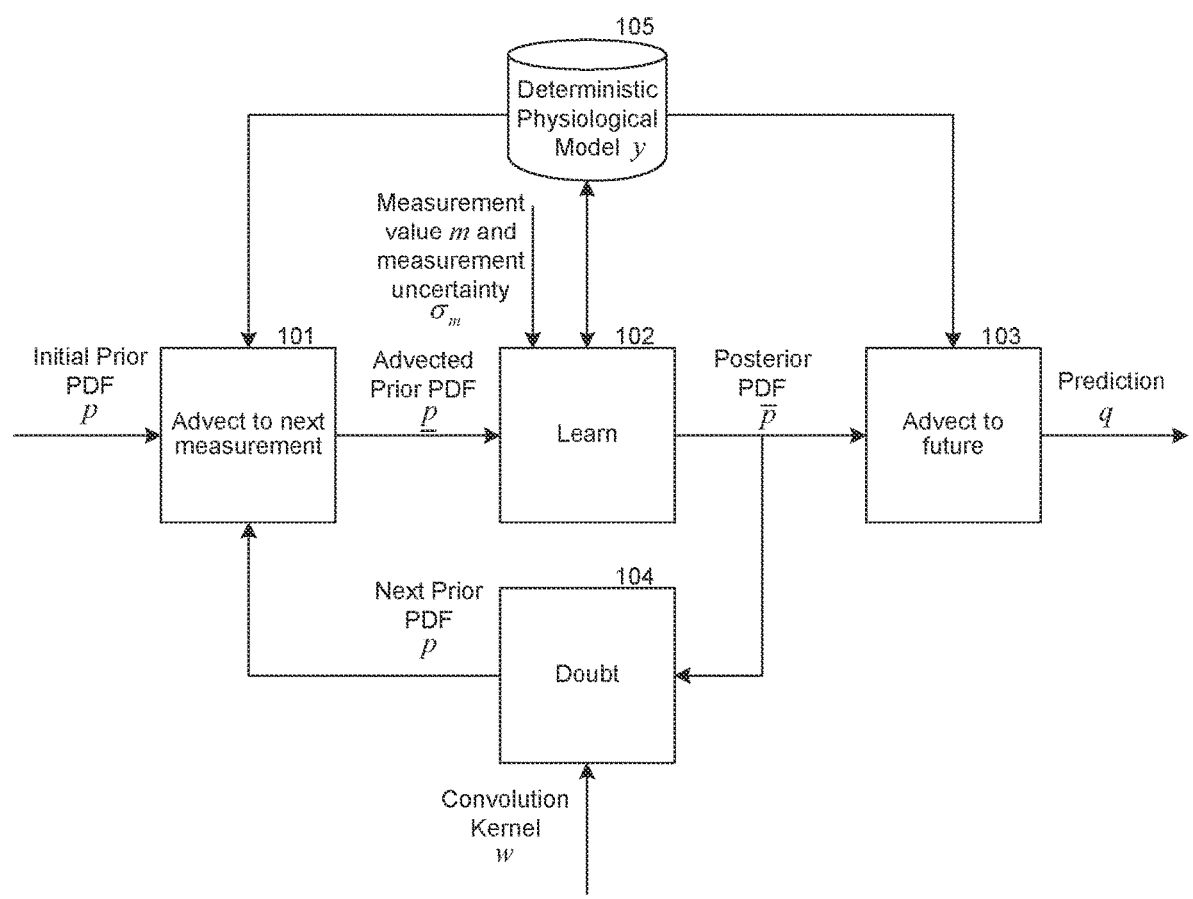
FIG. 1 is a block diagram that illustrates high-level components of the ABM system in some embodiments.

Methods and systems are provided that improve the accuracy of predicting the response of an individual patient to medical treatment. In some embodiments, a physiological response prediction ("PRP") system includes an advection-based modeling ("ABM") system, a component-based modeling ("CBM") system, and a component compilation ("CC") system. The ABM system models the evolution of a biological system (e.g., liver) over time using an advection-based process that is based on Bayesian learning to make predictions of the response of biological systems. The CBM system provides tools for a person to generate a componentized model of a biological system by connecting predefined components that model functions of biological systems. Some of the components may rely of the ABM system to predict a biological response. The CC system allows for a representation of a componentized model to be "compiled" into source code of a programming language.

In some embodiments, the CBM system provides a library of components for modeling certain biological processes of an organ (e.g., liver) such as the life cycle of the cells of the organ (e.g., hepatocytes) represented by a cell age distribution. Such a component may be generic in the sense that it can be used to model that certain biological process of various organs (e.g., liver, kidney, heart). The library may also contain components to generate inputs for and convert outputs of such a component. For example, a component may model the effect of a dose of a drug on the concentration of that drug in the blood stream. As another example, a component may combine inputs to generate an output such as to input cell divide rate and an age-independent cell death rate and output a cell aging rate. Each component has component code (e.g., C++ code) that models the biological process. In some cases, the modeling of a biological process may include a differential equation. The library may specify parameters that can be specified and state variables that can be initialized when executing a model to customize the behavior of the model (e.g., to a specific patient).

In some embodiments, a model developer generates a model of an overall of a biological system by selecting components from the library to implement the model and specifying interconnections between the components (e.g., output of one component is input to another component). The model developer may use a graphics tool to place and interconnect the components. Once a model is generated, the model developer may use the CC system to compile the model into implementation code (e.g., C++).

After a model is generated, control code may be used to execute the model to model the behavior of the biological system. To execute the model, the control code inputs a specification of parameters, state to be initialized, and one or more simulation times. The control code may invoke a differential equation solver specifying the parameter, state, and a simulation time to generate a solution (e.g., cell age distribution) for the model at that simulation time based on the differential equations represented by the implementation code (e.g., for modeling cell age distribution of an organ). A differential equation solver may be used to generate a solution for that simulation time. The differential equation solver may divide the simulation time into simulation steps (e.g., times) to generate solutions incrementally and then provide the final solution corresponding to the simulation time. The control code may also iteratively invoke the differential equation solver to generate solutions for successive simulation times. Prior to each iteration, the state may be modified to reflect, for example, an external influence (e.g., drug dosage).

In some embodiments, input to a biological process may be represented as continuous probability density function ("PDF"), rather than a discrete value. For example, the cell birth rate may be represented as a PDF. In such a case, the control code may, for each simulation time, invoke the differential equation solver multiple times each using a current discrete value sampled from the current PDF to generate a next discrete value. After the completing the invocations for a simulation time, the control code may generate a new PDF based on the next discrete values and the probability of current discrete values. The ABM system may then be used to generate an advected PDF from the new PDF using an advection equation. The advected PDF can then be used as the current PDF to generate the solution for the next simulation time.

ABM System

In some embodiments, an advection-based modeling ("ABM") system continuously evolves a probability density function ("PDF"), which is a joint PDF, for a characteristic relating to the physiological state of the biological system and its time-varying parameters. The PDF is evolved based on advection by solving an advection partial differential equation ("PDE") to learn parameter values for a model of the characteristic of the physiological state of the biological system. The physiological model has time-varying parameters for modeling the characteristic. For example, the biological system may be a liver and the state of the liver may be hepatocyte count. Since it is very difficult for the hepatocyte count to be measured directly (e.g., via a biopsy), the ABM system employs measurements of a characteristic, such as liver enzyme count in the blood, of the state of the liver to model the liver enzyme count from which the state of the liver can be inferred. The ABM system uses the continuously evolving PDF to make predictions about the characteristic of the state of the biological system. For example, a prediction may be the liver enzyme count at a future time.

The predictions of a characteristic of a state can be used to inform treatment for a patient. For example, the liver enzyme count may indicate whether a patient has an undesired level of hepatocytes. The ABM system can be used to predict the liver enzyme count at a prediction time. If the prediction liver enzyme count indicates that the patient will have an undesired level of hepatocytes, the drugs and/or dosing used to treat the patient can be modified to control the level of hepatocytes. For example, a model predictive control system can be used to determine dosing based on the predicted measurement to achieve a desired outcome. (See, e.g., Gaweda, A., Muezzinoglu, M., Jacobs, A., Aronoff, G., and Brier, M., "Model Predictive Control with Reinforcement Learning for Drug Delivery in Renal Anemia Management," Conf. Proc., Annual International Conference of the IEEE Engineering in Medicine and Biology Society IEEE Engineering in Medicine and Biology Society Conference, 2006.) Thus, the ABM system can be used as part of a method for treating a patient by predicting the characteristic, determining drug and dosing based on the characteristic, and administering the determined drug and dosing to the patient.

The ABM system may also be used to predict the characteristic of the state of the biological system even though the actual state is not observed. For example, the biological system may be erythropoiesis of a patient, the characteristic may be the red blood cell count, and the parameters of the physiological model may include the rate of red blood cell production and the rate of change in oxygen level. The ABM system can be used to predict the red blood cell count. A treatment plan for the patient may be based on the prediction of red blood cell count, rather than on an inference of the state based on red blood cell count. The red blood cell count can also be used to infer other characteristics such as the age distribution of red blood cell precursors and the concentration of erythropoietin.

The ABM system starts with an initial estimate of the state, the parameters, and the PDF. When a measurement of the state of the biological system is taken at a measurement time from a patient, the ABM system generates a new PDF based on the measurement and the physiological model. To generate the new PDF, the ABM system first generates an advected PDF by evolving the initial PDF (i.e., a prior PDF) to the measurement time by solving the advection PDE based on the physiological model of the biological system. The ABM system then generates a posterior PDF (i.e., the new PDF) by performing a learning process (e.g., Bayesian learning) that also generates new values for the parameters based on the advected PDF, the physiological model, and the measurement. Because new values for the parameters are generated, the physiological model is updated based both on the measurements of the patient and on the advected PDF. Over time, the physiological model and the PDF can more accurately represent the physiology of the biological system of an individual patient.

The ABM system can use the new PDF to make predictions of the state of the biological system at various times in the future. To make predictions, the ABM system evolves the new PDF to a prediction time by solving the advection PDE based on the physiological model of the biological system. The predictions are made based on the evolved new PDF and the physiological model of the biological system.

The ABM system may iterate the process of evolving the PDF using advection and learning to generate a new PDF for each subsequent measurement taken at a measurement time. During the next iteration, the ABM system may use the previous posterior PDF of the previous iteration as the next prior PDF for the next iteration with the next measurement to generate a new posterior PDF for making predictions. The ABM system may also set the next prior PDF to a modified version of the previous posterior PDF that is stretched to reflect uncertainty or doubt in the accuracy of the previous posterior PDF.

The ABM system is described primarily in the context of a biological system, such as the liver or erythropoiesis, of an individual organism. However, the ABM system may be used to model a variety of activities of different systems. Such systems may include geological systems (e.g., flow of lava, melting of polar ice caps, or occurrence of an earthquake), social systems (e.g., interactions between members of a social network and spread of information), environmental systems (e.g., growth of populations of animals and spread of toxic substances), financial systems (e.g., fluctuations in prices of securities and commodities), disease progression systems (e.g., spread of a disease in an individual or population), psychological systems (e.g., progress of a personality disorder), biological systems (e.g., heart, brain, liver, kidney, or gut tumor growth), and other physical and non-physical systems (e.g., dispersal of space debris). By providing an initial prior PDE, a model, and measurements for such system, the ABM system may be used to generate a posterior PDE for use in making predictions.

The ABM system is described primarily for the purpose of predicting a future state of a system. The ABM system may, however, be used for forensic purposes, that is, forming an estimate of what the state had been in the past. For example, if a population of people have died of a certain disease, the ABM system may be used to model the progression of that disease in each person based on the initial state of each person and measurements taken throughout the progression of the disease. The results may be used to identify more effective treatment regimes, to improve the model of how the disease progresses, and so on.

Because the ABM system factors in the measurements of the biological system of an individual organism, the ABM system evolves the PDF in a way that is tailored to that individual organism. For example, if the patient is being administered a drug that affects the production of red blood cells, the predictions using the PDF, which is evolved based on the measurements of the red blood cell counts taken while the patient is taking the drug, will reflect the effects of that drug overtime. In particular, the learning process will tend to evolve the parameters, such as rate of red blood cell production, to match that of the patient as indicated by the measurements. Thus, even if a parameter is initially set to a population-based value, it will evolve to match a value for the patient.

In some embodiments, during the time intervals between measurements, the ABM system continuously evolves the posterior PDF (i.e., generated based on the last measurement) using the advection PDE. When a measurement is taken, the ABM system suspends this continuous evolution. The ABM system uses the last posterior PDF as the prior PDF for the next iteration and generates the advected prior PDF. Because the learning process tends to narrow the posterior PDF, the confidence in the probabilistic understanding of the measurements and parameters increases. This narrowing, however, can slow the process of converging to true values and prevent the overall model from adapting to changes in the underlying parameters of the biological system. To reduce the narrowing, the ABM system stretches the posterior PDF after each learning step and uses that stretched posterior PDF as the prior PDF for the next iteration. This stretching is considered to systematically add doubt to the probability density function. Because the ABM system adds doubt, the rate of convergence to new values for the parameters and the adaptability of the ABM system is improved.

FIG. 1 is a block diagram that illustrates high-level components of the ABM system in some embodiments. When a measurement is received, an advect to next measurement component 101 accesses a deterministic physiological model y of data store 105 and receives an initial prior PDF p. The advect to next measurement component generates an advected prior PDF $\underline{p}$ by using the model y to advect the prior PDF p to the measurement time. For example, the deterministic physiological model y may be a model of a liver based on physiological dynamics, such as tumor size (i.e., state) and tumor growth rate (i.e., parameter). The initial prior PDF p may represent a measurement m of the tumor size at some prior time (e.g., measurement time of zero) based on a measurement uncertainty $\sigma_m$ (e.g., based on accuracy of the measurement) and tumor growth rate (e.g., population-based). After each measurement, the advect to next measurement component inputs a next prior PDF p (i.e., the previous posterior PDF) and generates the next advected prior PDF $\underline{p}$ using the current parameters of the physiological model.

A learn component 102 inputs the advected prior PDF $\underline{p}$ and the current measurement m and a measurement uncertainty $\sigma_m$ and applies a learning technique to learn new parameters and generate a posterior PDF $\bar{p}$ based on the inputs. The learn component updates the parameters in the data store.

An advect to future component 103 inputs the posterior PDF $\bar{p}$ and makes predictions q about the behavior of the biological system by advecting the posterior PDF $\bar{p}$ to the prediction time by solving the advection PDE based on the physiological model of the biological system. This advected posterior PDF is then used to make predictions of the state of the biological system at the prediction time. For example, if a heath care provider wants a prediction of the tumor size of the patent one week after the last measurement, the posterior PDF $\bar{p}$ is advected to a time of one week in the future (i.e., the prediction time) and that advected posterior PDF is used to make the prediction q of the tumor size.

A doubt component 104 inputs the posterior PDF $\bar{p}$ and a convolution kernel w and generates a next prior PDF p. The doubt component stretches the posterior PDF $\bar{p}$ to compensate for narrowing resulting from application of the learning technique. That stretched posterior PDF $\bar{p}$ is then used as the next prior PDF p for the next iteration.

In some embodiments, the advect to next measurement component advects the prior PDF p, from the previous measurement time to the current measurement time, by solving the advection PDE, which can be represented by the following equation:

$$\partial_t p + \partial_y \cdot (pV) = 0$$

$$V = \dot{y}$$

where $\partial_t p$ represents the partial derivative of the prior PDF p with respect to time t and $\nabla_y \cdot (pV)$ is the divergence of pV, the product of p and V, where V is a vector field representing the deterministic physiological model y. The advection PDE preserves the volume of the functions that it evolves. Thus, the advection PDE evolves PDFs, not just density functions. The advection PDE can be solved in various ways, such as:

1. Finding the closed-form solution.
2. Solving via the method of characteristics.
3. Solving via an upwind differencing scheme (e.g., such as a weighted essentially non-oscillatory ("WENO") scheme).

The time-varying PDF may be represented as $p: T \times Y \to \mathbb{R}^+$. For each time t, $p(t,-): \to \mathbb{R}^+$ represents the PDF. The initial PDF is represented as $p(t_0,-)$. The initial prior PDF p typically should not assign non-negative probabilities to physically impossible measurements and parameter values. As a result, lognormal PDFs may be preferable to normal PDFs.

A time-varying vector field is represented as $v: T \to y: Y \to T_y Y$, which defines the underlying physiological dynamics of the biological system. The vector field v defines the simultaneous evolution of both the state x and the time-varying parameters θ, represented as $y=(x,\theta)$. (The physiological model may also include parameters that are constant and thus not evolved.) The advect to next measurement component evolves the deterministic physiological model y assuming that the time-varying parameters are changing not via dynamics, just via learning updates, so that the time-varying parameters are piecewise constant in time. The deterministic physiological model y is the solution to a system of ordinary differential equations ("ODEs") as represented by the following equation:

$$\dot{y} = V(t, y)$$

The ODEs can be solved using standard stiff ODE solving software such as SUNDIALS from Lawrence Livermore National Laboratory. (See A. C. Hindmarsh, P. N. Brown, K. E. Grant, S. L. Lee, R. Serban, D. E. Shumaker, and C. S. Woodward, *SUNDIALS: Suite of Nonlinear and Differential/Algebraic Equation Solvers*, ACM Transactions on Mathematical Software, 31(3), pp. 363-396, 2005, which is hereby incorporated by reference.)

In some embodiments, the learn component calculates the posterior PDF $\bar{p}$ by applying Bayes' law to the advected prior PDF $\underline{p}$ using a likelihood function derived from the next measurement m and measurement uncertainty $\sigma_m$. The measurements are collected from the patient at scheduled times. The learn component uses a PDF $f(x; m, \sigma_m)$ for a univariate Gaussian random variable with a distribution of $N(m, \sigma_m)$, or a similarly parameterized lognormal, to calculate the posterior PDF $\bar{p}$. The formula for calculating the posterior PDF $\bar{p}$ is represented by the following equation:

$$\bar{p}(x, \theta) = \frac{p(x, \theta) \cdot f(x; m, \sigma_m)}{N}$$

$$N = \int_{X \times \Theta} p(x, \theta) \cdot f(x; m, \sigma_m) dx d\theta$$

In some embodiments, to calculate the prior PDF p, the doubt component adds doubt by "stretching" the posterior PDF $\bar{p}$ through convolution with the convolution kernel w. The convolution of functions $f$ and g is represented by the equation:

$$(f * g)(x) = \int f(\tau) \cdot g(x-\tau) d\tau$$

The integral may be multidimensional and can be calculated (1) using numerical routines or (2) in closed form of the functions $f$ and g that are particular PDFs. For example, if the functions are represented by the following equations:

$$f \sim N(\mu_f, \Sigma_f)$$

$$g \sim N(\mu_g, \Sigma_g)$$

then the closed form may be represented by the following equation:

$$f * g \sim N(\mu_f + \mu_g, \Sigma_f + \Sigma_g)$$

As another example, if the functions are represented by the following equations:

$$f \sim \exp(N(\mu_f, \Sigma_f))$$

$$g \sim \exp(N(\mu_g, \Sigma_g))$$

then the closed form may be represented by the following equation:

$$f * g \sim N(\mu_f + \mu_g, \Sigma_f + \Sigma_g)$$

with the constraints that $Ef = Eg$ where $Ef = \int (x \cdot f(x)) dx$. The convolution kernel w is a PDF over state x and the time-varying parameters θ that is uncorrelated with the posterior PDF $\bar{p}$. The convolution kernel w is thin with respect to state x and thin with respect to the time-varying parameters θ. The doubt component may use a convolution kernel w represented by the following equation:

$$w \sim N(\mu, \Sigma)$$

where $$\mu = 0, \quad \Sigma = \begin{pmatrix} 0 & 0 \\ 0 & \epsilon \end{pmatrix},$$

and $\epsilon$ is a small number. The next advected prior PDF $\underline{p}$ is represented by the following equation:

$$\underline{p} = \bar{p} * w$$

In some embodiments, the advect to future component advects the posterior PDF $\bar{p}$ to the measurement time using the advection PDE as represented by the following equations:

$$\partial_t p + \nabla_y \cdot (pV) = 0$$

$$V = \dot{y}$$

which are the same equations used by the advect to next measurement component.

The accuracy of the ABM system in predicting what an actual measurement will be can be demonstrated in various ways such as conducting a prospective, a retrospective, or clinical trial.

To conduct a prospective clinical trial, actual measurements are collected from a patient in real-time at collection times. The ABM system is used to personalize the parameter values of the ABM physiological model based on those actual measurements and then to evolve the PDF. The PDF is then used to generate predicted measurements for that patient at a prediction time in the future. At that prediction time, actual measurements are collected from the patient. When the predicted measurements accurately reflect (e.g., within an accuracy margin) the actual measurements at the predicted time, then the ABM system can be considered to be accurate.

To conduct a retrospective clinical trial, the actual measurements were collected from a patient at various collection times, including a prediction time. The ABM system is used to personalize the parameter values of the ABM physiological model based on those actual measurements with collection times that are before the prediction time. The ABM system then evolves the PDF. The PDF then is used to generate predicted measurements for that patient at the predication time. When the predicted measurements accurately reflect (e.g., within an accuracy margin) the actual measurements previously collected at the prediction time, then the ABM system can be considered to be accurate.

To conduct a simulated clinical trial, simulated measurements are generated at various simulation times, including a prediction time, using an ancillary physiological model to simulate measurements. The simulated measurements can be considered to be measurements of a simulated patient. The ABM system is used to personalize the parameter values of the ABM physiological model based on those simulated measurements with simulated times that are before the prediction time. The ABM system then evolves the PDF. The ABM system is used to evolve a PDF based on the simulated measurements with simulation times that are before the prediction time. The PDF then is used to generate predicted measurements at the prediction time. When the predicted measurements accurately reflect (e.g., within an accuracy margin) the simulated measurements for the prediction time, then the ABM system can be considered to be accurate.

If the ancillary physiological model has the same form as the ABM physiological model used by the ABM system, the ancillary physiological model will have parameter values that will characterize the behavior of the simulated patient. The ABM system is used to personalize the parameter values of the ABM physiological model based on those simulating measurements with simulated times that are before the prediction time. The ABM system then evolves the PDF. This personalizing and evolving is performed for various simulated times. If the parameter values for the ABM physiological model converge on the parameters for the ancillary physiological model, then the ABM system can be considered to be accurate. Thus, if the initial parameter values for the ABM physiological model are very different from those of ancillary physiological model, then accuracy of the ABM system is confirmed even when the initial parameter values for a patient are a poor guess of the actual parameter values for that patient.

Embodiments of the ABM system may be used as part of a method of treating a patient. To treat a patient, a care provider collects measurements of a characteristic of a state of a biological system of the patient. For example, the biological system may a liver, the state may be hepatocyte, and the characteristic may be liver enzyme count of the patient. The care provider then generates a prediction of a characteristic of a state of a biological system of the patient using a probability density function generated by the ABM system based on measurements of the characteristic collected from the patient and a physiological model of the biological system and based on advecting a prior PDF using the measurements and the physiological model. The care provider then infers from the prediction of the characteristic the state of the biological system. The care provider then determines course of treatment for the patient based on the inferred characteristic. The care provider then treats the patient in accordance with the course of treatment. The course of treatment is based on a model predictive control system. The course of treatment may relate to dosing of a drug.

Figure 2:
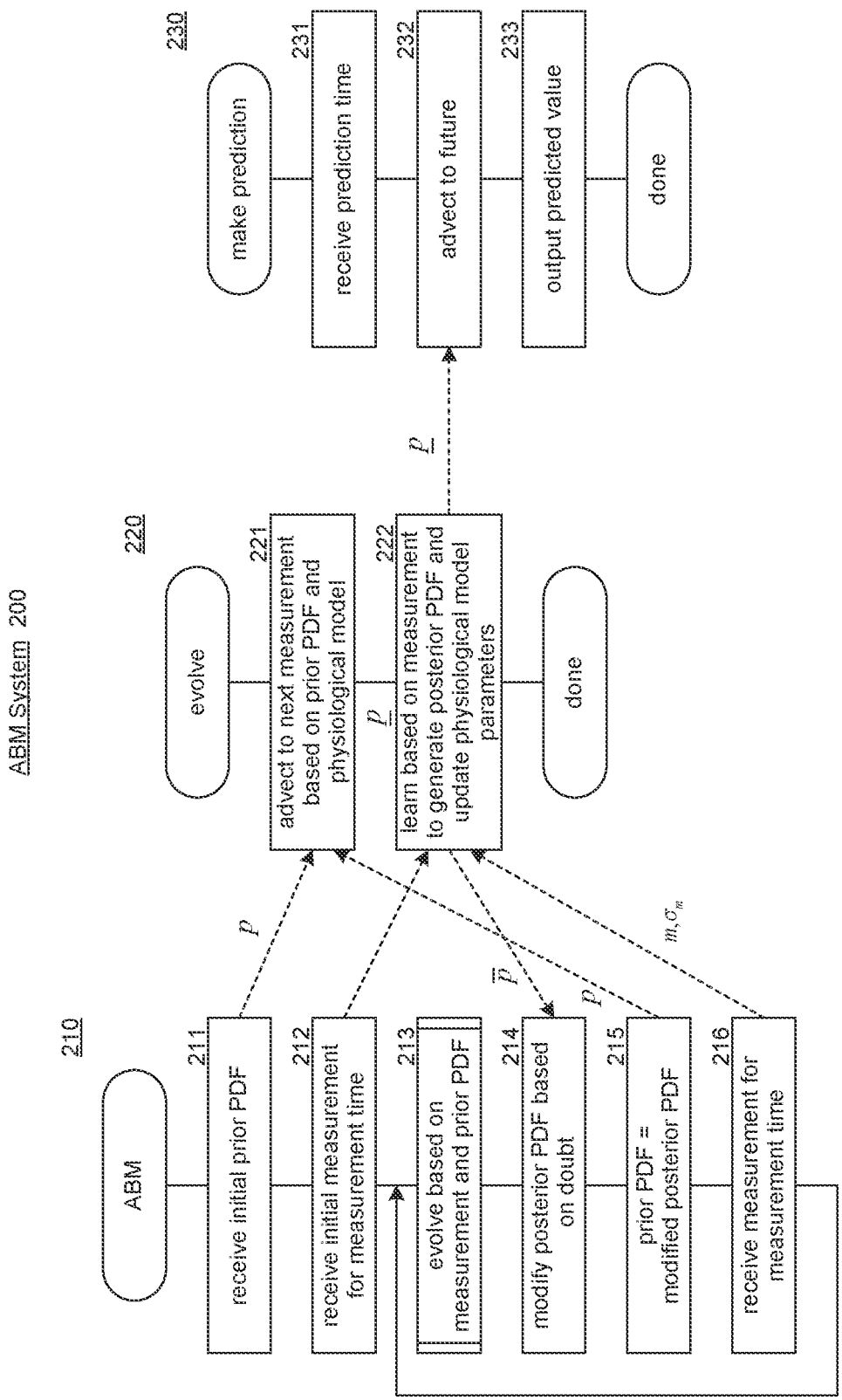
FIG. 2 includes flow diagrams that illustrate the overall processing of components of the ABM system in some embodiments.

FIG. 2 includes flow diagrams that illustrate the overall processing of components of the ABM system in some embodiments. An ABM component 210 controls the overall processing of evolving PDFs based on advection. An evolve component 220 controls the evolving of a prior PDF to a posterior PDF based on a measurement. A make prediction component 230 makes predictions by evolving a posterior PDF based on advection. In block 211, the ABM component receives an initial prior PDF for the initial state and time-varying parameters. In block 212, the ABM component receives an initial measurement representing the initial measurement time and a measurement uncertainty. In block 213, the ABM component invokes the evolve component to evolve the prior PDF based on the measurement, the current parameters of the physiological model, and the prior PDF to generate a posterior PDF. In block 214, the ABM component modifies the posterior PDF to factor in doubt in the learning of the parameters. In block 215, the ABM component sets the prior PDF to the modified posterior PDF. In block 216, the ABM component receives the next measurement and a measurement uncertainty for a measurement time. The ABM component then loops to block 213 to evolve the prior PDF based on the next measurement.

In block 221, the evolve component generates an advected prior PDF using the advection PDE. The directed dashed lines indicate data of the ABM component that is used by the evolve component. In block 222, the evolve component learns, based on the measurement, to generate a posterior PDF and completes. In block 231, the make prediction component receives a prediction time. In block 232, the make prediction component advects the posterior PDF to the prediction time. In block 233, the make prediction component outputs the predicted value based on the advected posterior PDF and then completes.

The computing devices and systems on which the PRP system may be implemented may include a central processing unit, input devices, output devices (e.g., display devices and speakers), storage devices (e.g., memory and disk drives), network interfaces, graphics processing units, accelerometers, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing devices may include desktop computers, laptops, tablets, e-readers, personal digital assistants, smartphones, gaming devices, servers, and computer systems such as massively parallel systems. The computing devices may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and include other storage means. The computer-readable storage media may have recorded upon or may be encoded with computer-executable instructions or logic that implements the PRP system. The data transmission media is used for transmitting data via transitory, propagating signals or carrier waves (e.g., electromagnetism) via a wired or wireless connection.

The PRP system may be described in the general context of computer-executable instructions, such as program modules and components, executed by one or more computers, processors, or other devices. Generally, program modules or components include routines, programs, objects, data structures, and so on that perform particular tasks or implement particular data types. Typically, the functionality of the program modules may be combined or distributed as desired in various embodiments. Aspects of the PRP system may be implemented in hardware using, for example, an application-specific integrated circuit ("ASIC").

In the following, an example use of the ABM system is provided based on a model for the constrained growth of a tumor using simulated measurements.

In this example, the underlying physiology of the biological system is constrained exponential growth of the state x, which represents the size of a tumor. The ABM system will evolve the biological system from time $t_0$ to a future time. So the evolution of the system will be governed by an ODE, as represented by the following equation:

$$\dot{x} = \theta x \left(1 - \frac{x}{k}\right) \quad (1)$$

where k is the maximum size of the tumor. This ODE has the following closed-form solution:

$$x(t; t_0, x_0) = \frac{kx_0 e^{\theta(t-t_0)}}{\left(k + x_0 \left(e^{\theta(t-t_0)} - 1\right)\right)} \quad (2)$$

where $x_0$ is the value of the state at a time $t_0$. The value for the initial state is $\bar{x}$. The value for the growth rate is $\bar{\theta}$. So, the value for the state x is represented by the following equation:

$$x(t; t_0, \bar{x}) = \frac{k\bar{x} e^{\bar{\theta}(t-t_0)}}{\left(k + \bar{x}\left(e^{\bar{\theta}(t-t_0)} - 1\right)\right)} \quad (3)$$

This equation represents the ancillary model. These true values for the parameters are used only to produce simulated measurements.

The simulation of the ABM process starts with a prior PDF for x and θ, evolves x using equation (3), and uses measurements to update the PDF. The expectation of the marginal density for x will converge to $\bar{x}$. The expectation for the marginal density for e will converge to $\bar{\theta}$. The measurement at any time t will be random perturbations of the state taken from equation (3).

The initial condition will be given at time $t_0$ and the measurements will be taken at times represented as:

$$t_i, i=1,2,\ldots,N. \quad (4)$$

The time intervals between measurements are represented as $$t_i = t_{i-1} + \Delta_i, i=1,2,\ldots,N. \quad (5)$$

Figure 3:
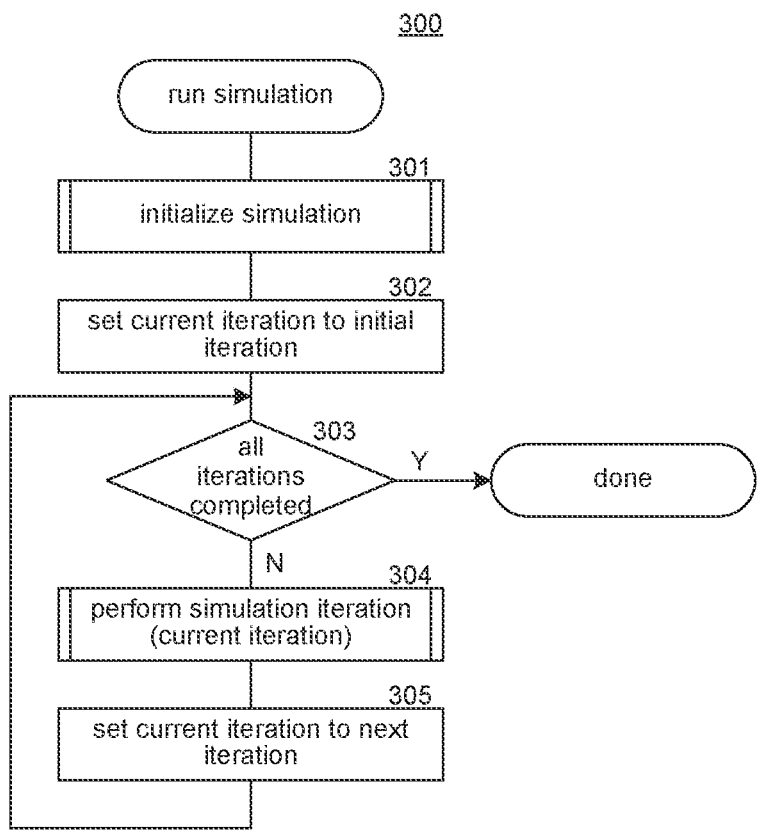
FIG. 3 is a flow diagram of a run simulation component. The run simulation component 300 controls the overall simulation.
Figure 4:
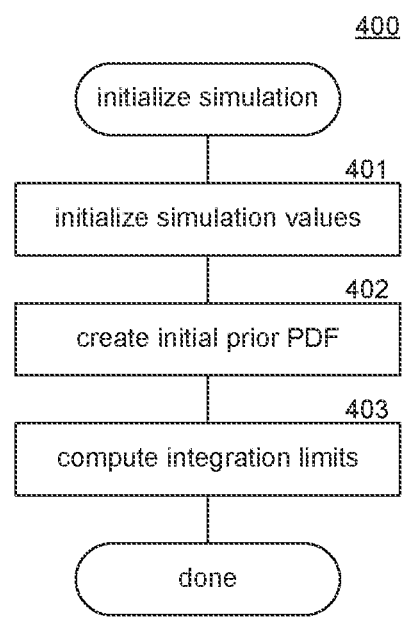
FIG. 4 is a flow diagram that illustrates the processing of an initialize simulation component.
Figure 5:
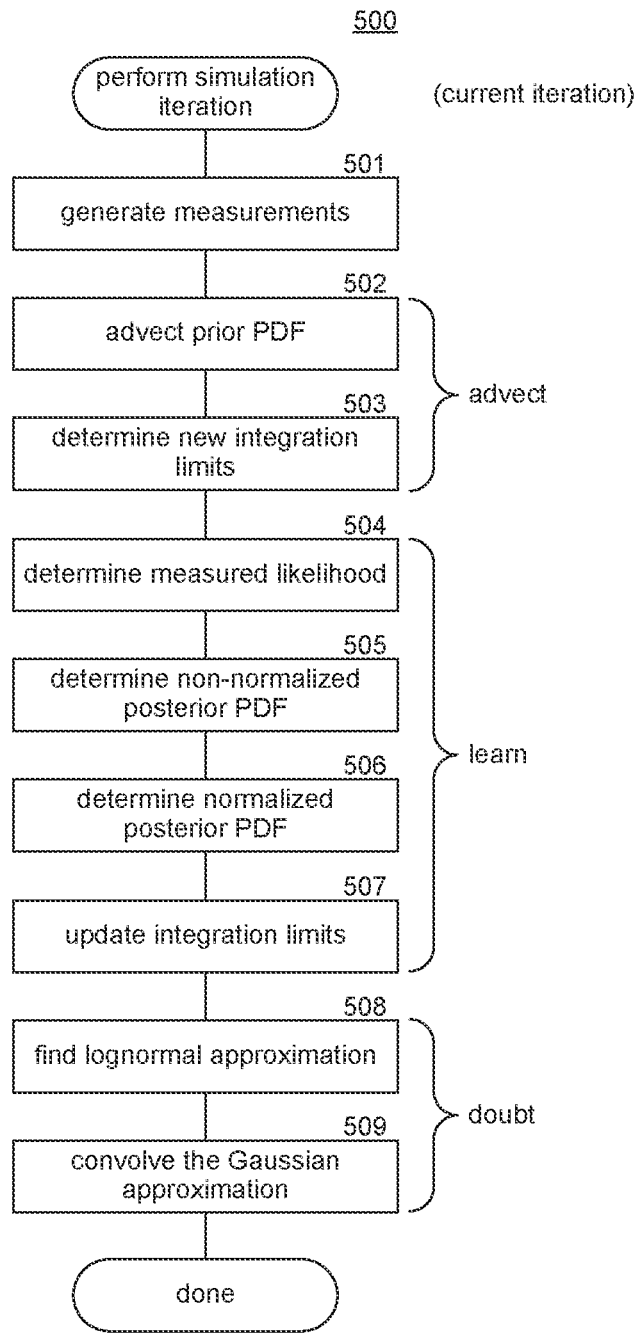
FIG. 5 is a flow diagram that illustrates the processing of a perform simulation iteration component.

FIGS. 3-5 are flow diagrams that illustrate the evolution of a PDF over time using simulated measurements. FIG. 3 is a flow diagram of a run simulation component. The run simulation component 300 controls the overall simulation. In block 301, the component invokes an initialize simulation component to establish the initial prior PDF and initial measurement. In block 302, the component sets the current iteration to the first iteration. In decision block 303, if all the iterations of the simulation have been completed, then the component completes, else the component continues at block 304. In block 304, the component invokes a perform simulation iteration component to perform the simulation for the current iteration. In block 305, the component sets the current iteration to the next iteration of the simulation and loops to block 303.

FIG. 4 is a flow diagram that illustrates the processing of an initialize simulation component. The initialize simulation component 400 generates initial simulation values and derives additional values from those initial values. In block 401, the component initializes the simulation values. In block 402, the component creates the initial prior PDF. In block 403, the component computes integration limits and then completes.

FIG. 5 is a flow diagram that illustrates the processing of a perform simulation iteration component. The perform simulation iteration component 500 performs the process for the current iteration. In block 501, the component generates the simulated measurements for the current iteration. In blocks 502-503, the component performs the advection to the next measurement. In block 502, the component advects the prior PDF to the advected prior PDF. In block 503, the component determines the new integration limits. Blocks 504-507 perform the learning to determine the parameter values and the posterior PDF. In block 504, the component determines the measured likelihood. In block 505, the component determines the non-normalized posterior PDF. In block 506, the component determines the normalized posterior PDF. In block 507, the component updates the integration limits. Blocks 508-509 correspond to the adjusting of the posterior PDF based on the doubt. In block 508, the component finds a lognormal approximation of the posterior PDF. In block 509, the component performs a convolution based on a Gaussian approximation and then completes.

Table 1 contains source code in the R programming language that implements the simulation.

TABLE 1

| INITIALIZATION |
| --- |

```
Integrator
int2lim.vV <- function(h, lo, hi) {
    h.v <- function(x) {matrix(h(t(x)), ncol=ncol(x))}
    hcubature(h.v, lowerLimit <- lo, upperLimit <- hi, vectorInterface = TRUE)&integral }
Find first and second moments of any density.
E1V <- function(f, i, lo, hi) {
    int2lim.vV( {function(xx) {xx[,i]*f(xx)}}, lo, hi ) }
E2V <- function(f, i, j, lo, hi) {
    in2lim.vV( {function(xx) {xx[,i]*xx[,j]*f(xx)}}, lo, hi ) }
```

TABLE 1-continued

```
Find the parameters of a lognormal density from the moments of a given (not necessarily
lognormal) density.
InormParamsV <- function (g, n, lo, hi) {
    gcoefs <- list( )
    Ey <- vector(length=n)
    mu <- vector(length=n)
    Eyy <- matrix(0, nrow=n, ncol=n)
    sigma <- matrix(0.,nrow=n, ncol=n)
    cov <- matrix(0.,nrow=n, ncol=n)
    for (i in 1:n){
        Ey[i] <- E1V(g,i,lo, hi)}
    for (i in 1:n){
        for (j in 1:n){
            Eyy[i,j] <- E2V(g,i,j,lo,hi)
            sigma[i,j] <- log(Eyy[i,j]/(Ey[i]*Ey[j])) }}
    for (i in 1:n){
        mu[i] <- log(Ey[i]) – sigma[i,i]/2.}
    for (i in 1:n){
        for (j in 1:n){
            cov[i,j] <- Ey[i]*Ey[j]*(exp(sigma[i,j])–1.) }}
    gcoefs[[1]] <- mu
    gcoefs[[2]] <- sigma
    gcoefs[[3]] <- Ey
    gcoefs[[4]] <- cov
    gcoefs }
Convolve two bivariate Guassian densities.
convGauss <- function( fcoefs, gcoefs ){
    hcoefs <- list( )
    hcoefs[[1]] <- fcoefs[[1]] + gcoefs[[1]]
    hcoefs[[2]] <- fcoefs[[2]] + gcoefs[[2]]
    hcoefs }
Compute a lognormal density value.
dmvlnorm <- function(y,mean,signma) (1/apply9y,1,prod))*dmvnorm(log(y),mean,sigma)
Compute the parameters of a non-correlated lognormal density from its moments; e is
a vector of expected values and c is a vector of variances.
from.moments <- function(e,c){
    vone <- rep(1, length(e))
    D <- log(c/(e^2) + vone)
    lcoefs <- list( )
    lcoefs[[1]] <- log(e) – D/2 #mu
    lcoefs[[2]] <- diag(D) #sigma
    lcoefs }
Find the mean (expectation) and the mode of a lognormal density.
emean ,- function(mu,sigma)
    exp(u + (1/2)*diag(sigma))
mode <- function(mu, sigma){
    vone <- rep(1., length(mu))
    c0 <- sigma %*% vone
    d0 <- mu-c0
    mode0 <- exp(d0) {
Dither a lognormal density with a normal density. make sure that the mean (expectation)
of the dithered density is the same as the mode of the original density.
dithr.lognormal.fix.mean <- function(lognormal.coefs, guassDithr.coefs){
    mu0 <- lognormal.coefs[[1]]
    dithrdcoefs <- convGauss(lognormal.coefs, guassDithr.coefs)
    sigma1 <- mu0 – (1/2)* diag(gaussDithr.coefs[[2]])
    function(y) dmvlnorm(y, mu1, signma1) }
The functions that define the constrained growth model.
# compute the growth in the forward direction
xf <- function(t,t0,x0,th,k) (k*xo*exp(th*(t–t0)))/(k + x0*(exp(th*(t–t0)) – 1.))
xdf <- function(delt,x0,th,k) (k*x0*exp(th*(delt)))/(k + x0*(exp(th*(delt)) – 1.))
# compute the growth in the reverse direction, i.e. look backwards
xpf <- function(delt,x1,th,k) (k*x1*exp(–th*delt))/(k + x1*(exp(–th*delt) – 1.))
# compute the spatial divergence piece of the solution to the advection equation
pplusf <- function(delt,xp,th,k) exp(–th*delt)*(1.+(xp/k)*(exp(th*delt) –1.))^2
Specify the particular values for constants for this simulation.
set.seed(12345)
dithr.coeffs <- list( )
sigmam <- 0.
sigmalik <- 20.
delt = 0.25
kch <- 800.
x0<- .5
to <- 0.
thch <- 4.
nsig <- 5.
num.half <- 6
num.all <- 2 * num.half
Create the initial prior.
```

TABLE 1-continued

```
ee <- c(1,6) #expectation of the lognormal
cc <- 7*c(.5,1) #covariance of the lognormal
logcoefs <- from.moments(ee,cc)
mu <- logcoefs[[1]] #of the underlying normal
sig <- logcoefs[[2]] #of the underlying normal
mux <- mu[1]
sigmax <- sig[1]
muth <- mu[2]
sigmath <- sig[2]
#compute the initial integration limits
nn<-20
llo <- c(max(0.00001,ee[1]-nn*cc[1]), max(0.00001, ee[2]-nn*cc[2]))
hhi <- c(ee[1]+nn*cc[1], ee[2]+nn*cc[2])
#the initial prior. Named dithrd to enable looping
dithrd <- function (y) dmvlnorm(y, mu, sig)
# compute the quantiles for the inital prior
coeffsV <- InormParamsV(dithrd,2,llo,hhi)
```

LOOP

```
for(i in 1:num.all){
  # Find the measured value
  x.hat.mean <- xfd(i*delt, x0, thch, kch)
  x.hat <- rnorm(n=1, mean=x.hat.mean, sd=sigmam)
  # Advect: Compute the advected prior
  # determine the new integration limits by advection
  llo <- c(.1*xfd(delt, llo[[1]], thch, kch), llo[2])
  hhi <- c(xfd(delt, hhi[1], thch, kch), hhi[2])
  priV <- function(xx) {xp <-xpf(delt,xx[,1],xx[,2],kch)
  dithrd(cbind(xp,xx[,2]))*pplus(delt,xp,xx[,2],kch)}
  coeffsV <- InormParamsV(priV,2,llo,hhi)
  Learn: Determine the measurement likelihood , then determine the non-normalized posterior
  lik <- function(x) dnorm(x, mean=x.hat, sd=sigmalik)
  nonnorm.postV <- function(xx) {priV(xx) * lik(xx[,1])}
  # Learn: Determine the normalized posterior
  v <- int2lim.vV(nonnorm.postV,llo,hhi)
  norm.postV <- function(xx) {(nonnorm.postV(xx))/v}
  norm.post.coeffsV <- InormParamsV(norm.postV,2,llo,hhi)
  # update the integration limitee <- norm.post.coeffsV[[3]]
  ee <- norm.post.coeffsV[[3]]
  cc ,- c(norm.post.coeffsV[[4]][1,1], norm.post.coeffsV[[4]][2,2])
  llo <- c(max(0.00001,ee[1]-nn*cc[1]), max(0.00001, ee[2]-nn*cc[2]))
  hhi <- c(min(ee[1]+nn*cc[1],kch), ee[2]+nn*cc[2])
  # Doubt: Use moments to find the lognormal approximation to the normalized posterior.
  norm.post.guassV0 <- function(xx) dmvlnorm(xx, mean=norm.post.coeffsV[[1]], sigma=norm.post.coeffsV[[2]])
  vnorm0 <- int2lim.vV(norm.post.guassV0,llo,hhi)
  norm.post.guassV <- function(xx) norm.post.guassV0(xx)/vnorm0 #adjust for possible truncation at the right
  # Doubt: Convolve the Gaussian dithering kernel. dithr.coeffs[[1]] <- c(0,0)
  dithr.coeffs[[2]] <- matrix(c(0,0,0,.009),ncol=2,nrow=2)
  dithrd0 <- dithr.lognormal.fix.mean(norm.post.coeffsV, dithr.coeffs)
  vdithrd0 <- int2lim.vV(dithrd0,llo,hhi)
  dithrd <- function (xx) dithrd0(xx)/vdithrd0 #adjust for possible truncion at the right end of the vector
  coeffsV <- InormParamsV(dithrd,2,llo,hhi)
}
```

CBM System

The CBM system provides components to model many different types of biological systems. The components can be used to model various aspects of biological systems such as:

1. the birth, aging, and death of cell populations
2. the effects of insults (e.g., toxic side effects of drugs) to cell populations
3. homeostasis of biological systems (e.g., to model metabolism repair)
4. characteristics of cell populations including:
   A. cells with a particular gene variant
   B. cells of parts of an organ (e.g., hepatocytes)
   C. cells of a whole organ (e.g., liver)
   D. cells of a collection of organs involved in a homeostasis loop
   E. cells of a whole organism The components can be used to describe biological systems representing physiology at a level where physiological measurements are part of the model, for example, liver enzyme measurements for modeling liver repair and damage and hemoglobin measurements for modeling homeostasis of red blood cell oxygen.

The CBM system does not rely on large datasets (i.e., Big Data-millions of samples) such as those used by machine learning techniques (e.g., neural networks). Rather, to create a model that uses Bayesian learning, the needed prior probability density function can be generated from a relatively small dataset (e.g., a few thousand samples). Also, a model for even a large-scale biological system requires few parameters (e.g., 10-20). The models, which can be complex components generated from primitive components, allow for identification of a component of a model that is the cause of unexpected behavior of a model and effective representation of internal structure of a biological system.

Figure 6:
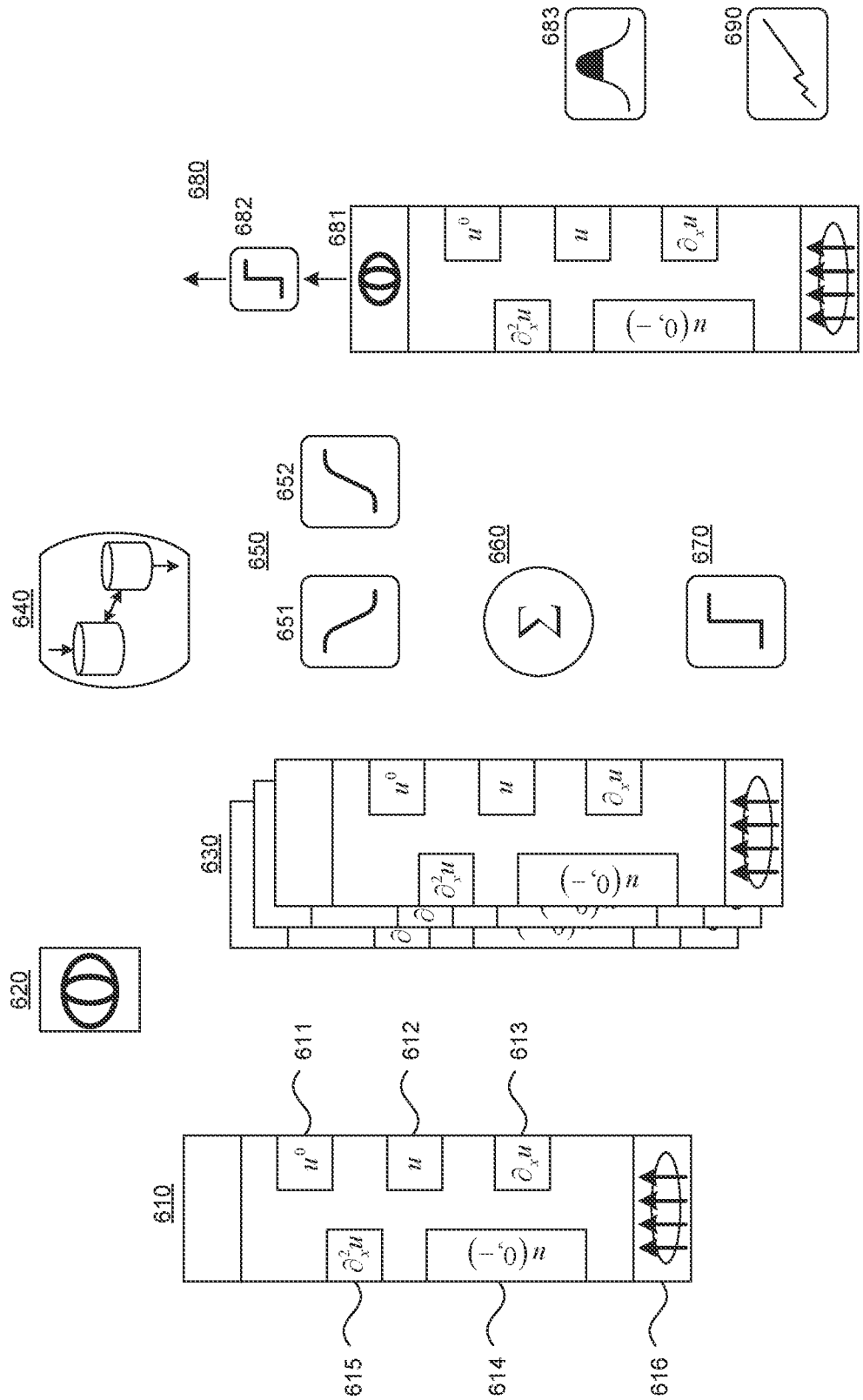
FIG. 6 illustrates primitive component of the CBM system in some embodiments.

FIG. 6 illustrates primitive component of the CBM system in some embodiments. These components include a single-species aging ("SA") component 610, an observer ("O") component 620, a linked species aging ("LA") component 630, a pharmacokinetics ("PK") component 640, a response curve ("RC") components 650, a linear combination ("LC") component 660, and a clamp ("TH") component 670. The components can be combined to represent an area under the curve ("AuC") component 680 and a non-monotonic response curve ("RE") component 690.

In some embodiments, the SA component is adapted to model the aging dynamics of a population of cells using partial differential equations ("PDEs"). The PDEs have a time dimension with time greater than 0 and range dimension of normalized age from a birth age of 0 to death age of 1. The SA component inputs an age-dependent death rate 611 (e.g., older cells may die at a faster rate than younger cells), a cell reduction rate 612 (i.e., death rate and divide or split rate), an aging rate 613, an initial cell distribution 614 (e.g., count per age), a diffusion coefficient 615, and a cell birth rate 616. The SA component generates the next current cell age distribution 617. The SA component maintains the current cell age distribution as state for use in the next step of the simulation. The SA component implements equations for modeling the next cell age distribution that may be independent of the organ being modeled and used to simulation function of the organ. Equations 6-9 Illustrate the mapping to the next cell age distribution.

$$u_t + \alpha u_x = \delta_b \partial_x^2 u - \beta u \quad (6)$$

$$(\alpha u - \delta_b u_x)|_{x=0^+} = F_{in} \quad (7)$$

$$(\alpha u - \delta_b u_x)|_{x=1^-} = F_{out} \quad (8)$$

$$u|_{t=t_0} = \psi \quad (9)$$

| Symbol | Time Variance | Description |
|---|---|---|
| $\delta_b$ | invariant | diffusion coefficient |
| $\alpha$ | discrete | aging rate |
| $t_0$ | discrete | initial time |
| $\Psi$ | discrete | initial cell age distribution |
| $\beta$ | continuous | age-independent death rate |
| $F_{in}$ | continuous | total flux at left-boundary (age x = 0⁻) |
| $F_{out}$ | continuous | total flux at right-boundary (age x = 1⁺) |
| u | continuous | current cell age distribution (not exported, see Observers below) |

In some embodiments, the CBM system may employ a weighted essentially non-oscillatory ("WENO") algorithm of Method of Lines algorithm to solve the differential equations. With these algorithms, the diffusion coefficient should be relatively small compared to the aging rate and the death rate. The diffusion coefficient is used because some biological systems do not preserve discontinuities. The equations of the SA component are defined as part of the CBM system for modeling the dynamics of a cell population. The SA component with the specified equations may be used when model the cell population of a variety of organs including liver, kidney, and so on.

Figure 7:
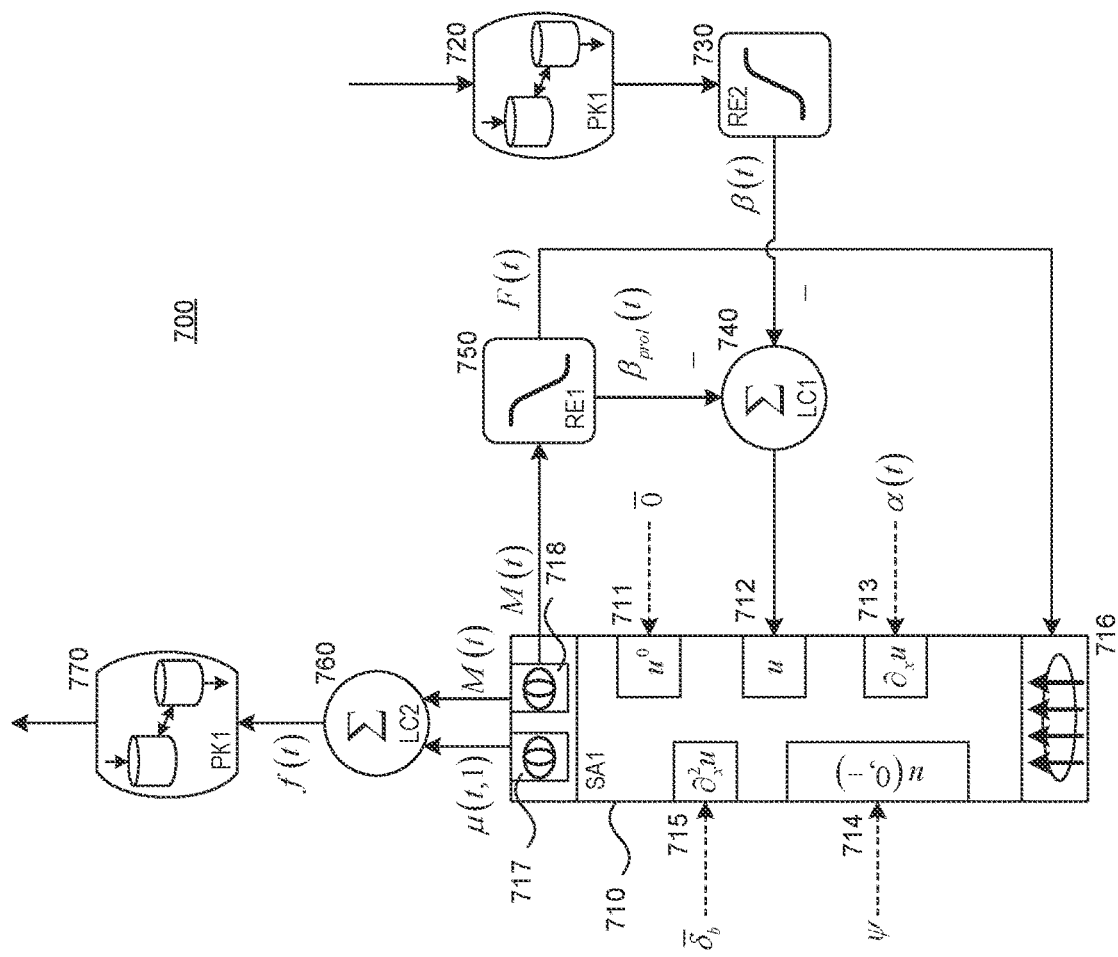
FIG. 7 is a block diagram that illustrates a model of the effects of acetaminophen on liver cell population in some embodiments.

In some embodiments, the CBM system does not allow the next cell age distribution to be accessed directly by other components. So, the CBM system provides an O component (which may be considered a sub-component that defines a function as illustrated in FIG. 7) to be specified by an instantiation of the SA component to generate an output (an observable) of a function of the next cell age distribution that can be directly accessed by components. An O component may not maintain any state. An SA component may have multiple O components. An O component may also be illustrated as a component that is separate from the SA component that inputs the next cell age distribution that is output by the SA component.

In many biological systems, the birth, aging, and reduction rates of one cell species affect the birth, aging, and reduction rates of another cell species. The LA component is a generalization of the SA component in which the current cell age distribution is represented as a vector and the rates are represented as square matrices. The off-diagonal elements of these matrices encode the coupling of rates between two cell species.

A PK component represents the pharmacokinetics of a drug such as the mapping of a dosage of acetaminophen to concentration level in the blood. PK components are generally represented by a first-order ordinary differential equation with a low state dimension (e.g., 2-5). The equations are generally stiff and described as a compartment model with some phenomological compartments. The equations of the PK components of a model are specific to the pharmacokinetics of the drug whose effects are modeled by the PK component and provided by the developer of the model.

An RE component represents an expected response curve. For example, an RE component may input a total number of cells for a species and output the expected growth rate, which may be small when the total number is large and large when the total number is small. The equations of the RE components of a model may be specific to the organ being modeled and provided by the developer of the model. An example response curve may be represented by a one-dimensional Hill component as represented by equation 10.

$$y = a + (b-a)\frac{(x-\tau)^n}{K_A^n + (x-\tau)^n} \quad (10)$$

| Symbol | Time Variance | Description |
|---|---|---|
| a | invariant | minimum |
| b | invariant | maximum |
| $\tau$ | invariant | offset |
| n | discrete | Hill coefficient |
| $K_A$ | discrete | x at half saturation, à la EC50 |
| x | continuous | input |

An LC component outputs a weighted linear combination of its inputs. For example, a dead cell count may be represented as a linear combination of total cell count and the cell count of cells at the maximum age. The equations of the LC components of a model may be specific to the organ being modeled provided by the developer of the model. An example linear combination may be represented by equation 11.

$$y = \sum_i^n w_i x_i \quad (11)$$

| Symbol | Time Variance | Description |
| --- | --- | --- |
| n | invariant | number of inputs |
| {$w_i$} | discrete | family of n weights |
| {$x_i$} | continuous | family of n inputs |

A TH component ensures that an input is greater that minimum threshold and less than a maximum threshold by clamping the input to between the minimum and maximum thresholds. The equations of the TH components of a model may be specific to the organ being modeled provided by the developer of the model. An example clamping of the input may be represented by equation 12.

$$y = \max(a, \min(x, b)) \quad (12)$$

| Symbol | Time Variance | Description |
| --- | --- | --- |
| a | discrete | minimum |
| b | discrete | maximum |
| x | continuous | input |

An RC component is monotonic with a low-response region at one end and a high response region at another end. An RE component 690, in contrast, represents the non-monotonic behavior of a hermetic system in which some of the summands are shifted, which is represented by the T parameter of the RC component. An RE component represents a collection of RC components whose outputs are input to an LC component. The equations of the RC components of a model may be specific to the organ being modeled provided by the developer of the model.

In pharmacodynamics, an AuC component may include a threshold. The AuC of a cell population is represented by the total cell population. An AuC component represents a combination of an SA component 681 with an O component of an aging primitive and a TH component 682 with a one-sided threshold. An AuC component may be illustrated as icon 683. The equations of the AuC components of a model may be specific to the organ being modeled provided by the developer of the model.

FIG. 7 is a block diagram that illustrates a model of the effects of acetaminophen on liver cell population in some embodiments. (The effects of acetaminophen on the liver are described in Moyer et al, "Acetaminophen-NAPQI Hepatotoxicity: A Cell Line Model System Genome-Wide Association Study," Toxicol Sci. 2011 March; 120(1): 33-41, which is hereby incorporated by reference.) In this model, PK component 720 inputs a dosage of acetaminophen, and PK component 770 outputs a predicted level of liver enzymes in the blood stream. The model also includes SA component 710, RE component 730, LC component 740, RE component 750, and LC component 760. SA component 710 inputs data 711-716 as described in reference to SA component 610. The SA component also includes O components 717 and 718. O component 717 inputs the next current cell age distribution and outputs the number of liver cells at the maximum age $\mu(t,1)$, which represents number of cells at age 1 (end of lifecycle) at time t. O component 718 inputs the next current cell age distribution and outputs the total number of cells M(t). PK component 720 input an acetaminophen dose and outputs acetaminophen concentration in the blood. RE component 730 inputs acetaminophen concentration in the blood and outputs an age-independent death rate $\beta(t)$, which is a function of the concentration of acetaminophen. RE component 750 inputs the total number of cells and outputs cell divide rate (proliferate) $\beta_{prol}(t)$ and the cell birth rate F(t). The cell birth rate is based on the cell divide rate and represents rate of new cell creation, which is based on the total number of cells (e.g., less cells result in a higher divide rate). LC component 740 inputs the cell death rate and the cell divide rate and outputs the cell reduction rate $\beta(t)+\beta_{prol}(t)$. LC component 760 inputs the number of cells at the maximum age $\mu(t,1)$ and the total number of cells M(t) outputs the total number of dead cells F(t). PK 770 inputs that total number of dead cells F(t) and outputs the liver enzyme level.

The function of PK component 720 for modeling the level of acetaminophen in the blood may be represented by the following equations (see Moyer for understanding of terms):

$$\frac{C_{gut}}{dt} = -k_a C_{gut}$$

$$\frac{C_1}{dt} = -k_{12}C_1 + k_{21}C_2 - k_{10}C_1 + Fk_a C_{gut}$$

$$\frac{C_2}{dt} = k_{12}C_1 - k_{21}C_2$$

$$\frac{C_{NAPQI}}{dt} = \text{pk}_{10}C_1 - k_{bin}C_{GSH}C_{NAPQI}$$

$$\frac{C_{GSH}}{dt} = k_{GSH} - (k_{bin}C_{NAPQI} + k_{el,GSH})C_{GSH}$$

The function of RE component 730 may be represented by the following equation:

$$\beta(t) = \frac{\beta_{max} C_{NAPQI}^n}{EC_{50}^n + C_{NAPQI}^n}$$

The function of RE component 750 may be represented by the following equations:

$$\beta_{prol}(t) = \beta_{prol_0} \frac{a_0}{1 + \left(\frac{M(t)}{\theta}\right)^n}$$

$$\theta = \frac{1}{(a_0 - 1)^{1/n}}$$

$$f(t) = 2\beta_{prol}(t) \cdot M(t)$$

The function of LC component 760 may be represented by the following equation:

$$f(t) = \beta(t)M(t) + \alpha u(t,1)$$

The function of PK component 770 may be represented by the following equations:

$$\frac{C_{AST}}{dt} = \delta_{AST} f - k_{el,AST} C_{AST}$$

$$\frac{C_{ALT}}{dt} = \delta_{ALT} f - k_{el,ALT} C_{ALT}$$

$$\frac{F_{VII}}{dt} = k_{VII} M(t)/\hat{H} - k_{el,VII} F_{VII}$$

-continued $$\frac{F_{II}}{dt} = k_{II}M(t)/\hat{H} - k_{el,II}F_{II}$$

$$INR = \exp(-0.251*\log(F_{II}) - 0.296*\log(F_{VII}) + 1.168)$$

The functions of SA component 710 include the cell birth rate function as represented by the following equation:

$$(\alpha(t)u(t,x) - \delta_b \partial_x u(t,x))|_{x=0^+} = F(t)$$

and the next cell age distribution function as represented by the following equation:

$$\partial_t u(t,x) + \alpha(t)\partial_x u(t,x) = \delta_b \partial_x^2 u(t,x) - (\beta(t) + \beta_{prol}(t,x))u(t,x)$$

$$t \in [t_0, t_{cmax}], 0 < x < 1$$

The function of observer 718 is cell count function as represented by the following equation:

$$\int_0^1 u(t,x)dx$$

The PRP system employs an ODE solver (e.g., SUN-DAILS) is used to solve these equations for each time step of a simulation. For example, given a dose of acetaminophen for a patient, the equations can be solved for different times to model the effect on liver enzymes at those times. As new doses are administered, the solution for the subsequent times will factor in that new dose.

The use of a component-based model simplifies the implementation of a model based in part because each component implements a well-defined function and the behavior of a component can be more easily verified and corrected during implementation (e.g., debugging of code that implement the behavior). For example, the behavior of PK component 720 can be tested independently of any model that uses that component. Thus, a library of components with corresponding code that implements each component may be created and used when generating models. To create a model, a model developer may select components from the library and/or create new components, specify model-specific parameters for the equations of the components, and define the interconnection of the outputs to inputs of the components. The model developer generates step code to implement a step of the simulation associated with a step time. The step code includes the component code of the components and control code (provided by the developer of the model) that controls the invocation of the components during a step of the simulation. Referring to FIG. 7, such control code would input a dose of acetaminophen and invoke the code of PK component 720 providing the dose as an input parameter and receiving the concentration of acetaminophen in the blood as an output parameter. The control code would invoke code of the RE component 730 providing the concentration as an input parameter and receiving the age-dependent death rate as an output parameter. The control code would then invoke the LC component 740 providing the age-dependent death and the cell divide rate (of the prior step) and receiving a cell reduction rate. When the component code of component implements a PDE, the control code invokes an ODE solver passing the component code to generate the results, which are the outputs of the component code.

Gut Model

The CBM system may be used to model the function of the gut, for example, to predict gut damage. The SA component may be implemented to model enterocytes lifespans.

Homeostasis in the intestinal epithelium may be represented by the following partial differential equation:

$$\partial_t b(t,s) + \alpha_{ent}(t)\partial_s b(t,s) = -\beta(t)b(t,s)$$

$$t \in [t_0, t_{max}]$$

where b is a cell age distribution function, $\alpha$ is cell aging rate, $\beta$ is cell death rate, A is input and output flux, and $b_0$ is initial cell age distribution. The following boundary and initial conditions may be applied:

$$\alpha_{ent}(t)b(t,s)|_{s=0^+} = \alpha_{prec}(t)a(t,s)|_{s=S_{max,prec}} = A(t)$$

$$b(t_0,s) = \Psi(s) = b_0(s),$$

where A(t) is the TADCs (precursors or transit amplifying daughter cells) flux from the precursor compartment: A: $\mathbb{R}_+ \to \mathbb{R}$; $\psi(s)$ is the boundary condition (state vector of the dynamical system $b_0$): $\psi: \mathbb{R} \to \mathbb{R}$; unknown function b(t,s), b: $\mathbb{R}_+ \times \mathbb{R} \to \mathbb{R}$, is the enterocytes density distribution function with units of dimension: cell number (#) per unit volume (L), per unit of physiological age (s). Coefficients $\alpha_{ent}(t)$ and $\beta(t)$ are piecewise constant functions with respect to t, $\alpha_{ent}: \mathbb{R}_+ \to \mathbb{R}$ and $\beta: \mathbb{R}_+ \to \mathbb{R}$.

A model similar to the enterocytes lifespan model may be implemented for the enterocyte precursors. An age-structured model for enterocyte precursors is similar to one for mature enterocytes as represented by the following equation:

$$\partial_t a(t,s) + \alpha_{prec}\partial_s a(t,s) = \beta_{prec}(t,s)a(t,s), t \in [t_n, t_{n+1}], s \in [0, S_{max,prec}]$$

where $\alpha_{prec} \in \mathbb{R}$ is velocity of maturation that is assumed constant; and $\beta_{prec}(t,s)$, $\beta_{prec}: \mathbb{R}_+ \times \mathbb{R} \to \mathbb{R}$, is a variable coefficient that describes precursors proliferation and death rate due to administered chemotherapy agents, which has the following form:

$$\beta_{prec}(t,s) = \mu - A_{tox}(t)$$

and the following boundary and initial conditions:

$$\alpha_{prec}(t)a(t,s)|_{s=0^+} = A_{surv}(t)E_{ENT}(t),$$

$$a(t_0,s) = \psi(s) = a_{0(1)}(s).$$

The enterocytes homeostasis may be controlled by the number of remaining enterocytes. This process may be modeled by incorporating a feedback in the proliferation rate as represented by the following equation:

$$\beta_{prol}(t) = \beta_{prol_0}\frac{a_0}{1 + \left(\frac{M(t)}{\theta}\right)^n}$$

where $\beta_{prol_0}$ is a steady state proliferation rate, $\alpha_0$ is an acceleration number of the proliferation rate for maximum damage, $M(t) = \int_0^1 b(t,x)dx$ is the total normalized enterocyte count at time t, M=1 at the steady state, and $\theta$ is a cell count normalization factor, which to ensure the appropriate proliferation rate at the steady state may be set to:

$$\theta = \frac{1}{(a_0 - 1)^{1/n}}.$$

Kidney Model

The CBM system may be used to model the function of the kidney, for example, to predict kidney damage. The SA component may be implemented to model nephron lifespans, which may be described by the following differential equation:

$$\partial_t n(t,s) + \alpha(t,s)\partial_s n(t,s) = \delta_b \partial_s^2 n(t,s) - \beta(t)n(t,s)$$

$$t \in = [t_0, t_{max}]$$

$$s \in [0, S_{max}]$$

u is an age-like distribution function for the nephron density distribution, $\alpha$ is a rate function for the sclerotic index (functioning as an aging-like function) which is a Hill's function response curve, and $\beta$ is a death rate function The glomerular filtration rate function GFR is an observer. The following boundary and initial conditions are applied:

$$(\alpha(t,x)n(t,s) - \delta_b \partial_s n(t,s))|_{s=0+} = n_0(0)\delta(t_0)$$

$$n(0,s) = n_0(s)$$

unknown function n(t,s), n: $\mathbb{R}_+ \times \mathbb{R} \to \mathbb{R}$ is the nephron density distribution function with units of dimension: unit number (#) per unit volume (L), per unit of sclerosis index (s), coefficients $\alpha(t,s)$, $\beta(t)$, $\delta_b$ are piecewise constant functions with respect to t, Physiologically, $\alpha$ controls the progression of the sclerotic index increase, $\beta$ describes the rate of drug insults to the kidney due to toxicities, $\delta_b$ describes age related accumulation of sclerotic scars. The total glomerular filtration rate (GFR) is computed as $$GFR(t) = \int_0^{S_{max}} gr(s)n(t,s)ds$$

where gr(s) is the glomerular filtration rate of a single nephron. Parameter $\alpha$ may be represented by a Hill's function. It is low for small values of index s and saturates at values close to $$S_{max}.$$

Prior are identified for Hill's function parameters from the population analysis, and the values tabulated for the gr (s) function.

Component Compilation System

In some embodiments, the CC system complies a component-based model to generate implementation code that implements the model. The model, referred to more generally as a network, specifies components and interconnection of the components. For example, FIG. 7 illustrates such a model. A definition of a component includes component code that implements the functions (also referred to as behavior) of the component and specifies variables such as parameter, input, output, and state variables and their associated variable types. A parameter variable is set when a component is initialized and does not change. A state variable corresponds to a value that is maintained internally by the component across steps of the simulation. An input variable and an output variable are inputs to and outputs of the component. The CC system may provide a component library that contains the definition of each component that is available to be used in a model. Continuing with the example, PK component 720 includes component code that implements the pharmacokinetics relating to acetaminophen as specified by the associated equations and specifies an input parameter of drug dose and output parameter of acetaminophen concentration. To compile a model, the CC system generates implementation code that includes the component code of each component of the model and additional code to set the input parameters based on the connections between the components and any external inputs. The generated implementation code can be used by a differential equation to simulate or execute the model.

In some embodiments, a model may be specified in a variety of ways. For example, the component library may include an icon for each component that provides a visual representation of that component. A developer may use a graphic tool (e.g., Visio or a special-purpose tool) to place components and interconnect the components to generate a visual representation of the model. The CC system may also provide a tool to validate the "syntax" of a model to ensure, for example, that inputs are only connected to outputs (or an external input), that the type of an input is the same type of the output to which it is connected, and so on. The visual representation of a model as depicted, for example, in FIG. 7 may be very useful to a developer to help in refining (e.g., debugging) the model. A model may also be specified using declarative or imperative statements that specify the components and their interconnection as described below.

In some embodiments, the CC system may be used to compile models specifying components and their interconnections for a variety of activities including those described above for the ABM system. Some of the components (e.g., an SA component) model stateful systems whose evolution of state is represented by a differential equation. Such components provide an equation that computes the right-hand side ("RHS") of an ordinary differential equation ("ODE"), which is a partial derivative of its state with respect to time. The CC system supports of use of a "stiffness" annotation provided by a developer to factor an RHS into explicit and implicit terms so that an implicit-explicit solver can be applied to the compiled code.

In some embodiments, each component is defined using properties as described in the following table:

| Name | Description | Specification |
| --- | --- | --- |
| Parameter variables | Values to tailor operation of the component and typically established when the component is instantiated | Name and type |
| Input variables | Values that input to the component | Name and type |
| State variables | Values that represent the current state of the component | Name, type, and dimension of each state variable |
| Output variables | Values that are available to be used as an input to a component | Name and type |
| RHS | Right hand side of an ODE that governs the evolution of the state variable | Code of RHS of ODE equation |

-continued

| Name | Description | Specification |
| --- | --- | --- |
| Output functions | Functions that generate the output variables | Code for each output variable |
| Function Dictionary | Dictionary of functions that additively mutate part of the state | Name and code for each function |

The properties of a component may be specified using the syntax of the Haskell programming language. The component code may be specified in the Python programming language.

In some embodiments, the CC system employs various constructs to specify the components and interconnections of the components including those of the following table.

| Construct | Description |
| --- | --- |
| Juxtapose | Form a new network containing two networks that are not connected |
| Place | Add an instance of a component to a network |
| Wire | Connect an input of a component to an output of a component |
| Seal | Hide all outputs of a network except specified outputs |

A network can be represented formally by the following tuple:

$$(P, I, S, O, W, U, E_{rhs}, E_{obs})$$

with its elements defined by the following table:

| Element | Description |
| --- | --- |
| P | tuple of parameter variables |
| I | tuple of input variables |
| S | tuple of state vector variables |
| O | tuple of output variables |
| W | set of pairs an output and an input |
| U | set outputs that identify unsealed output variables |
| R | set of pairs outputs that identifies renamed sealed variables |
| $E_{rhs}$ | an expression to reference variables in P, I, and S that denotes a tuple of shap S of state tangent vectors |
| $E_{obs}$ | an expressing indices to reference variables in P, I, and S that denotes a tuple of shape O of outputs |

The juxtaposition of two networks concatenates (operator #) the tuples of the networks and forms a tuple that is a concatenation (operator $\#_E$) of the expressions of the networks. The juxtaposition of network 1 and network 2 can be represented as follows:

$$P = P_1 \# P_2$$

$$I = I_1 \# I_2$$

$$S = S_1 \# S_2$$

$$O = O_1 \# O_2$$

$$W = W_1 \cup W_2$$

$$U = U_1 \cup U_2$$

$$R = R_1 \cup R_2$$

$$E_{rhs} = E_{rhs,1} \#_E E_{rhs,2}$$

$$E_{obs} = E_{obs,1} \#_E E_{obs,2}$$

The wiring of output o to input i adds (o,i) to W. Output o is an element of U represented by o∈U and input i is an element of I that is not already wired to an output as represented by i∈(I−{j|(−,j)∈W}).

The sealing of an output o removes the output from U. If the output o is also renamed as output o', output o' is added to O and the pair (o,o') is added to R to indicate that output o' is an alias of output o.

The CC system may generate implementation code of a network that includes the global variables and functions as represented by the following table:

| Name | Description |
| --- | --- |
| parameters | tuple containing the name of each parameter |
| taps | tuple containing the name and vector dimension of each state vector |
| observables | tuple containing name and state of each observable (output of an O component) |
| explicitRHS(t, p, s, sdot) | function to compute explicit RHS of the ODE given time t, parameters p, state s, and RHS ODE sdot |
| implicitRHS(t, p, s, sdot) | function to compute implicit RHS of the ODE given time t, parameters p, state s, and RHS ODE sdot |
| observe(t, p, s) | function computing the observable tuple |
| depositable | dictionary mapping the name of a depositable to its function |

Figure 8:
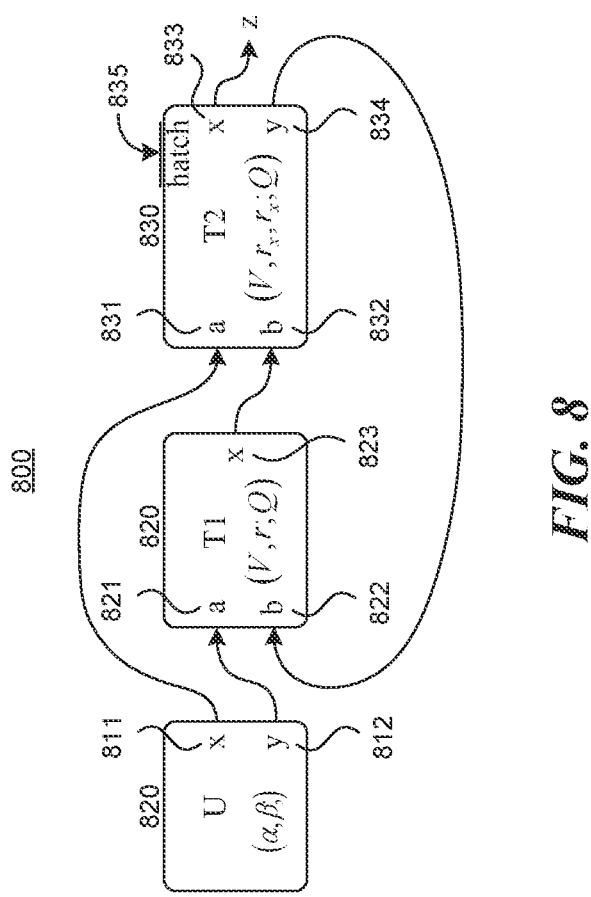
FIG. 8 illustrates an example network to model the operation of salt tanks.

FIG. 8 illustrates an example network to model the operation of salt tanks. In this example, the component library includes an upstream component and a tank component. The upstream component models the generation of one or more streams of saline solution and outputs the salt concentration of each outgoing stream (e.g., ounces/gallon) based on a parameter specifying salt concentrations for each stream. A tank component models the change in salt concentration of a tank of saline solution with one or more incoming streams of saline solution and one or more outgoing streams of saline solution. The tank component inputs the salt concentration of each incoming stream and outputs the salt concentration of each outgoing stream. The tank component includes parameters representing volume of the tank and the rate of outflow of saline solution (e.g., gallons/minute) for each outgoing stream. The tank component includes a state representing quantity of salt within the tank. The tank component specifies a function to model the depositing of quantities of salt into the tank at various times via a hatch at the top of the tank. The tank component specifies an equation for calculating the output for each outgoing stream based on the rate of outflow of a stream and the quantity of salt in and volume of the tank. The tank component also specifies an ODE RHS for the change in quantity of salt over time and the sum of the salt concentration of the incoming streams minus the sum of the salt concentrations of the outgoing streams. The tank component assumes the volume is a constant so that the sum of the rates of inflow of the incoming streams equals the sum of the rates of outflow of the outgoing streams.

Referring back to the example network, network 800 models two saline tanks and two upstream sources of saline. One upstream source is fed into the first tank, and the other upstream source is fed into the second tank. The first tank has an outgoing stream that is fed into the second tank. The second tank has one outgoing stream that is fed into the first tank and a second outgoing stream that is output of the model. Network 800 includes upstream instance U 810 of an upstream component, a first instance T1 820 of a tank component, and a second instance T2 830 of a tank component. Output 811 of the upstream instance is connected to the input 831 of the second tank instance, and output 812 of the upstream instance Is connected the input 821 of the first tank instance. Output 823 of the first tank instance Is connected to input 832 of the second tank instance. Output 834 of the second tank instance is connect to input 822 of the first tank instance. Output 833 of the first tank instance is an output of the model.

The Instances of the components are defined by the following tables

Upstream

| Parameters | α: salt concentration via x | β: salt concentration via y |
|---|---|---|
| Inputs | None | |
| States | None | |
| Output | X | y |
| RHS | None | |
| Output function | Outputs constant α for x | Outputs constant β for x |
| Hatch function | None | |

TankType1

| Parameters | V: volume | r: rate of x |
|---|---|---|
| Inputs | a | b |
| States | Q: concentration | |
| Output | x | |
| RHS | dQ/dt = a + b − x | |
| Output function | x = r*Q/V | |
| Hatch function | None | |

TankType2

| Parameters | V: volume | $r_x$: rate of x | $r_y$: rate of y |
|---|---|---|---|
| Inputs | a | b | |
| States | Q: concentration | | |
| Output | X | | y |
| RHS | dQ/dt = a + b − x − y | | |
| Output function | x = $r_x$ * Q/V | | y = $r_y$ * Q/V |
| Hatch function | amt: added to tank | | |

Network 800 may be specified declaratively using the following sequence as represented by the following table:

| Construct | Description |
|---|---|
| place U Upstream | Add component 810 |
| place T1 TankType1 | Add component 820 |
| wire U.y to T1.a | Add connection 812 |
| place T2 TankType2 | Add component 830 |
| wire U.x to T2.a | Add connection 811 |
| wire T2.y to T1.b | Add connection 821 |
| wire T1.x to T2.b | Add connection 832 |
| seal z = T2.x | Seal all but output 831 |

Each of the constructs adds a component to the network, connects an input to an output, or indicates an output that is not sealed. In the following table, the constructs of the network are presented with a description of the effect on the tuple that describes the network.

| Construct | Tuple Effect |
|---|---|
| place U Upstream | $P_0 = I_0 = S_0 = O_0 = ()$<br>$W_0 = U_0 = R_0 = \emptyset$<br>$P_1 = (U.alpha, U.beta)$<br>$O_1 = (U.x, U.y)$ |
| place T1 TakeType1 | $P_2 = (U.alpha, U.beta, T1.V, T1.r)$<br>$I_2 = (T1.a, T1.b)$<br>$S_2 = (T1.Q)$<br>$O_2 = (U.x, U.y, T1.x)$ |
| wire U.y to T1.a | $W_3 = \{ (U.y, T1.a) \}$ |
| Place T2 TankType2 | $P_4 = (U.alpha, U.beta, T1.V, T1.r,$<br>$T2.V, T2.rx, T2.ry)$<br>$I_4 = (T1.a, T1.b, T2.a, T2.b)$<br>$S_4 = (T1.Q, T2.Q)$<br>$O_4 = (U.x, U.y, T1.x, T2.x, T2.y)$ |
| wire U.x to T2.a | $W_5 = \{ (U.y, T1.a), (U.x, T2.a) \}$ |
| wire T2.y to T1.b | $W_6 = \{ (U.y, T1.a), (U.x, T2.a), (T2.y, T1.b) \}$ |
| wire T1.x to T2.b | $W_7 =$<br>$\{ (U.y, T1.a), (U.x, T2.a), (T2.y, T1.b),$<br>$(T1.x, T2.b) \}$<br>fully wired:<br>$\{ k \mid 0 \leq k < |I_7| \} = \{ j \mid (\_, j) \in W_7 \}$<br>no seals:<br>$U_i = \{ k \in \mathbb{Z} \mid 0 \leq k < |O_i| \}$ for $0 \leq i < 8$<br>$R_i = \emptyset$ for $0 \leq i < 8$ |

-continued

| Construct | Tuple Effect |
|---|---|
| seal z = T2.x | $O_8$ = (U.x, U.y, T1.x, T2.x, T2.y, z)<br>$U_8$ = {z}<br>$R_8$ = { (T2.x, z) } |

In some embodiments, to simplify the implementation of the CC system, the elements of the W, U, and R tuple may include de Bruijn references to I and O tuples. For example, in the comment $R_8$={(T2.x,z)}, the pair may be represented as (3, 5) where T2.x is the element of O indexed by 3 and z is the element of O indexed by 5.

In some embodiments, a network may be described using imperative pseudocode, rather than the declarative constructs as represented by the following.

```
seal
    (λo. { z=o.T2.x } )
    (fix
        (λfeedback.juxtapose
            {
                U=Upstream{ }
                T1=TankType1 {a=U.y, b=feedback.T2.y}
                T2=TankType2 {a=U.x, b=T1.x}
            }
        )
    )
``` where fix is a fixed-point combinator for anonymously recursive functions and the braces { . . . } introduce tuples with named fields.

$(i\_0 + i\_1 - p[1]*S[0]/p[0],)$ $(p[1]*s[0]/p[0],)$

In some embodiments, the CC system generates the Python code for network 800 as illustrated in the table below. For sake of illustration, some minor revisions to code have been made, for example, to eliminate dead code and improve variable names. Also, the code indicates to solve the ODEs for T1 explicitly and T2 implicitly even though they are similar ODEs.

```
 1    parameters = (
 2        "U.alpha", "U.beta", "T1.V", "T1.r",
 3        "T2.V", "T2.rx", "T2.ry" )
 4    taps = (("T1.Q", 1), ("T2.Q", 1) )
 5    # ^ ^ (name,dimension) ^ ^
 6    unsealed_observables = ("a",)
 7
 8    def explicitRHS (t,p,s, sdot) :
 9        sdot.fill (0)
10
11        # observables
12        o_1 = p[1]       # U.y
13        o_2 = p[3] * s[0] / p[2]       # T1.x
14        o_4 = p[6] * s[1] / p[4]       # T2.y
15
16        # wires
17        i_0 = o_1        # T1.a
18        i_1 = o_4        # T1.b
19
20        # explicit RHS
21        sdot[1] = i_0 + i_1 - o_2
22
23    def implicitRHS(t,p,s, sdot) :
24        sdot.fill (0)
25
26        o_0 = p[0]       # U.x
27        o_2 = p[3] * s[0] / p[2]       # T1.x
28        o_3 = p[5] * s[3] / p[4]       # T2.x
29        o_4 = p[6] * s[3] / p[4]       # T2.y
30
31        i_2 = o_0        # T2.a
32        i_3 = o_2        # T2.b
33
34        # implicit RHS
35        sdot[3] = i_2 + i_3 - o_3 - o_4
36
37    def observe (t,p,s) :
38        o_3 = p[5] * s[3] / p[4]       # T2.x
39
40        # renaming seal
41        o_5 = o_3        # z
42
43        # unsealed observations
44        return (o_5,)
45
46    def T2_hatch(t,p,s,amt_ounces) :
47        # deposit
48        s[3] += amt_ounces / p[4]
49
50    depositables =
51        { "T2.hatch": T2_hatch }
```

Figure 9:
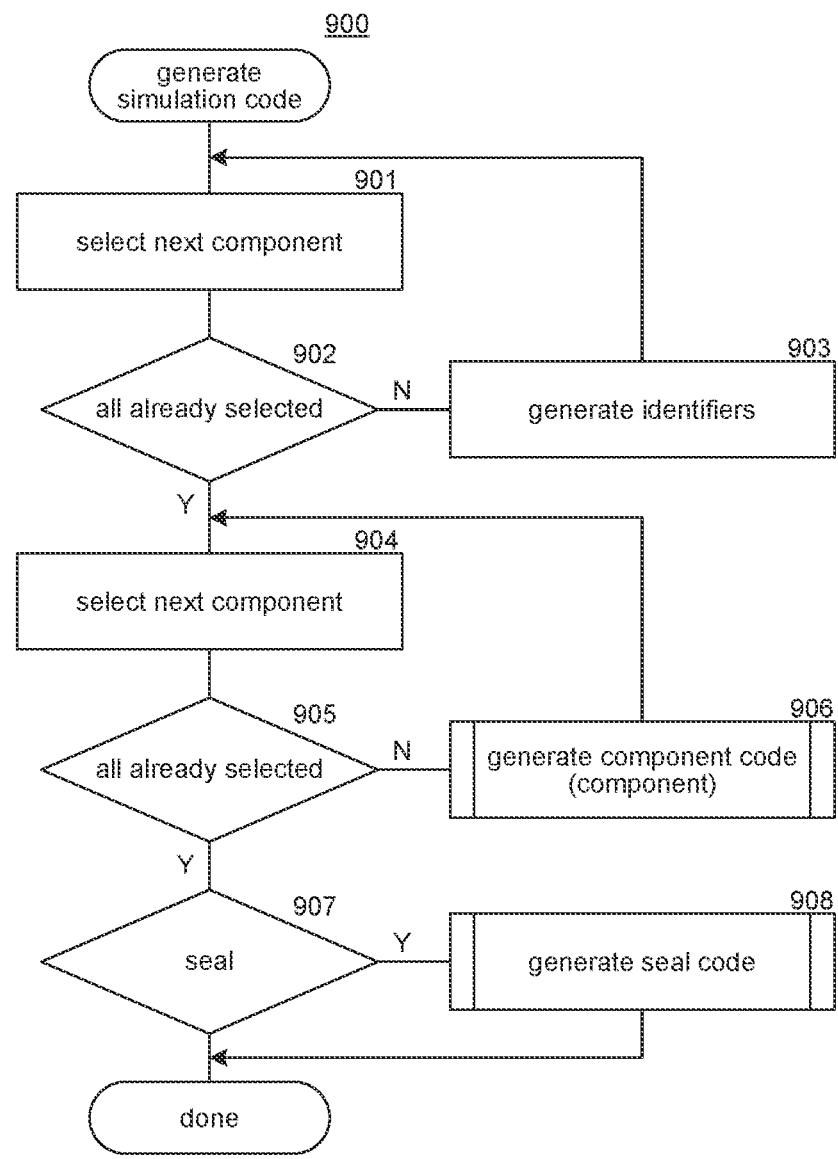
FIG. 9 is a flow diagram that illustrates processing of a generate simulation code module of the CC system in some embodiments.

FIG. 9 is a flow diagram that illustrates processing of a generate simulation code module of the CC system in some embodiments. A generate simulation code module 900 is invoked to generate compiled code for a network of components. The definition of the network may be preprocessed to identify components and interconnection of outputs to inputs. In blocks 903-904, the module loops generating identifiers for variables of the simulation code. Referring to lines 1-3 of the example code, the identifier for a variable may be the name the component followed by the name of the variable specified in the definition of the component. For example, in line 2, the variable for the parameter of the upstream "U" component named "alpha" is "U.alpha." Lines 2-3 illustrate a "parameters" statement that is an array that contains the names of the parameters, which are input to the simulation and specify the characteristics of the components such as quantity of a tank. Line 4 illustrates a "taps" statement that is an array that contains the names of the state of the components. The module also generates names for the input and output variables such as "i_0" corresponding to input "T1.x." The names for the input variables may be simply "i_x" where x is a number that is incremented for each input of each component in the order the components are specified in network definition and in the order of the inputs for each component. The module adds the "parameters" and "taps" statements to the simulation code. In blocks 904-906, the module loops invoking a generate component code module for each component to generate the simulation code for that component. The module may only generate a subroutine (e.g., "explicit RHS") for components that specify an ODE RHS. The input variable of an input of an ODE RHS component is set to the output function of the output of the wired-from component to which it is connected. Such an output function may depend on an input of the wired-from component. So, the module may process the output functions recursively to ensure that all variables needed for an input of the ODE RHS are set before setting the value of that input. In decision block 907, if the network definition includes a seal statement to seal the outputs except for certain output, the module continues at block 908, else the module completes. In block 908, the module invokes a generate seal code module to generate the simulation code to affect the unsealing of the designated outputs.

Figure 10:
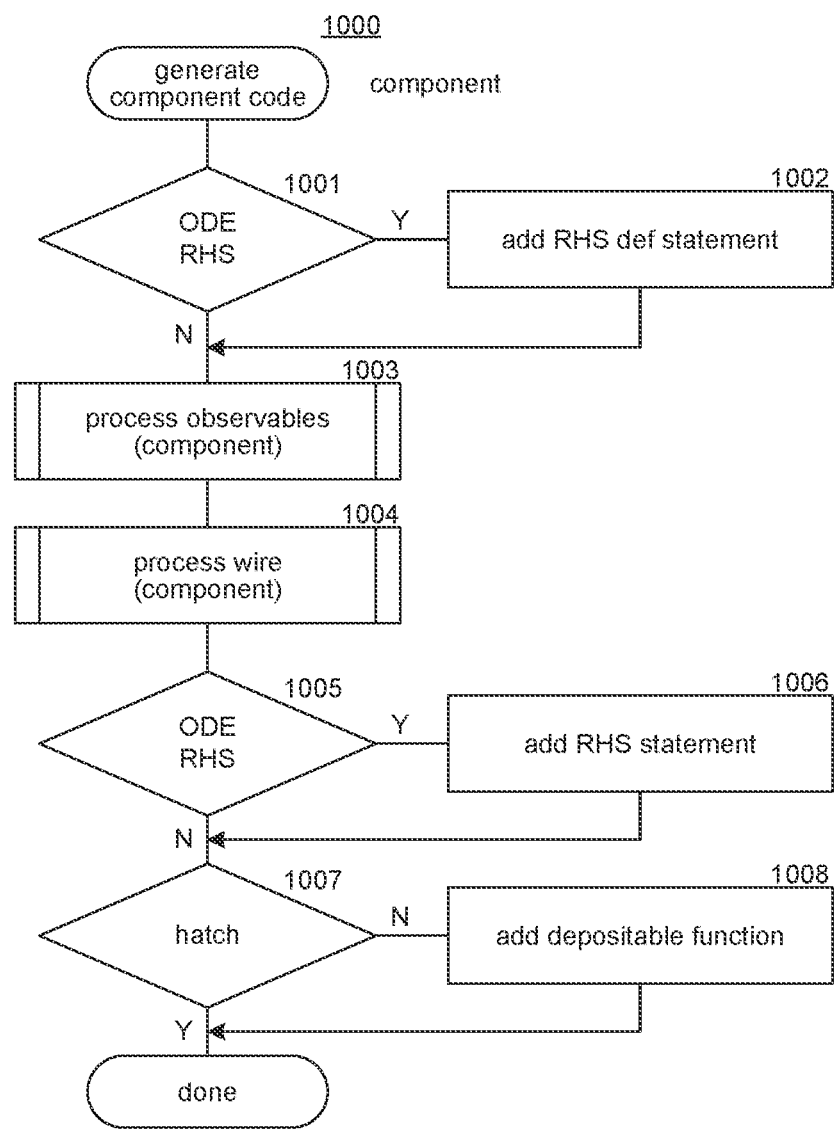
FIG. 10 is a flow diagram that illustrates the processing of a generate code module of the CC system in some embodiments.

FIG. 10 is a flow diagram that illustrates the processing of a generate code module of the CC system in some embodiments. A generate code module 1000 is passed an indication of a component to generate simulation code for the component. In decision block 1001, if the component includes an ODE RHS, then the module continues at block 1002, else the module continues at block 1003. In block 1002, the module adds an RHS definition statement to the simulation code. As discussed above, component code may alternatively not be generated for each component that does not include an ODE RHS. In such a case, the output functions of those components can be added in line with the component code for an ODE RHS. In block 1003, the module invokes a process observables module passing an indication of a component to generate the simulation code for the observables of the component. In block 1004, the module invokes a process wire module passing an indication of the component to process connections to the inputs of the component. In decision block 1005, if the component includes an ODE RHS, then the module continues at block 1006, else the module continues at block 1007. In block 1006, the module adds an RHS statement to the simulation code. In decision block 1007, if the component specifies a hatch, then the module continues at block 1008, else the module completes. In block 1008, the module adds a hatch function to the simulation code. Lines 46-48 illustrates a hatch function to add of an amount of salt to tank T2 through its hatch. The hatch function includes a statement to increase the state for salt concentration. The module also adds a mapping of the name of the hatch function to a mapping of names to the hatch functions so that code that calls a hatch function can use the name specified in the component definition.

Figure 11:
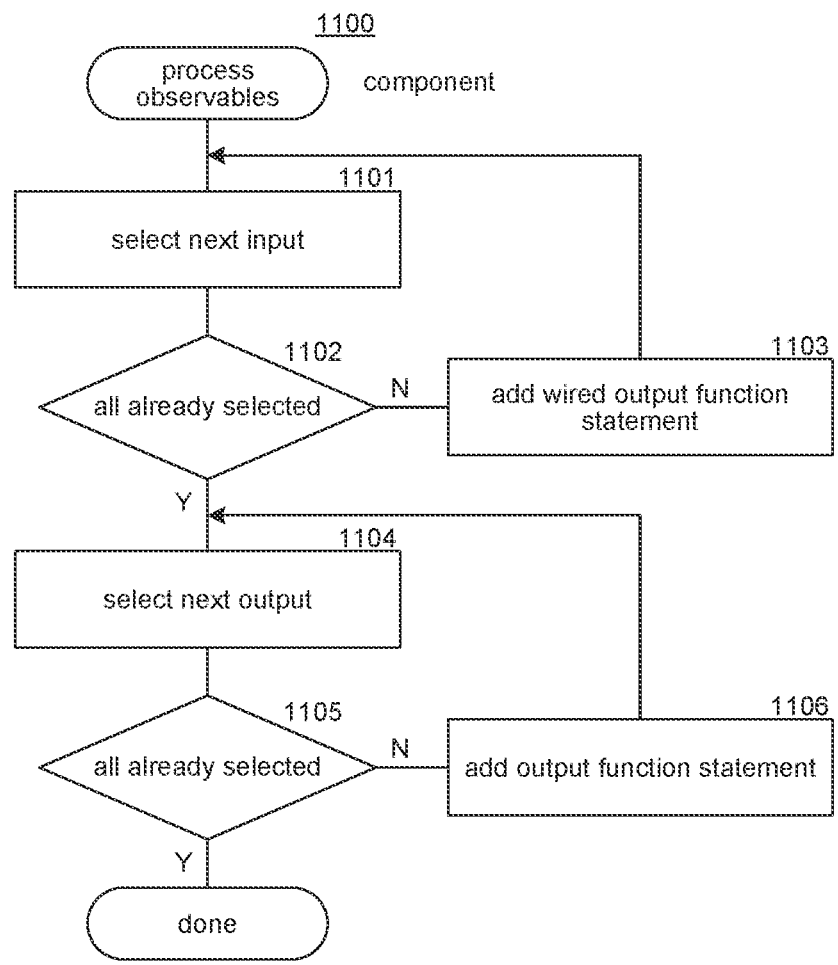
FIG. 11 is a flow diagram that illustrates processing of a process observables module of the CC system in some embodiments.

FIG. 11 is a flow diagram that illustrates processing of a process observables module of the CC system in some embodiments. A process observables module 1100 is passed an indication of a component to generate statements relating to observables or outputs related to the component. Lines 12-14 of the sample simulation code illustrates the observable statements for tank T1 component. Lines 12 and 14 illustrate statements to generate the output that is input to the tank T1 component. Line 13 illustrates a statement to generate the output of the tank T1 component. In blocks 1101-1103, the module loops selecting each input of the component and generating an output function statement corresponding to the output to which the selected input is wired or connected. In blocks 1104-1106, the module loops selecting each output of the component and generating an output function statement for each output. The module then completes.

Figure 12:
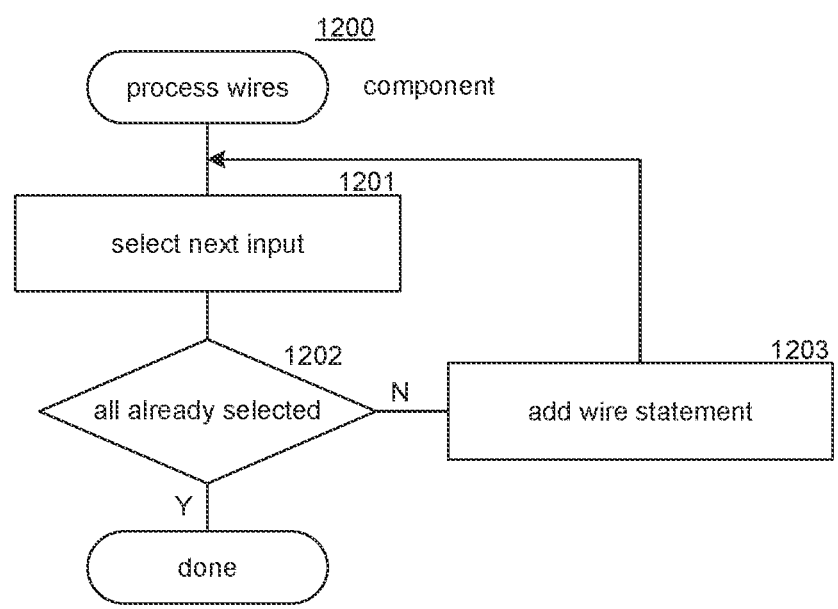
FIG. 12 is a flow diagram that illustrates the processing of a process wires module of the CC system in some embodiments.

FIG. 12 is a flow diagram that illustrates the processing of a process wires module of the CC system in some embodiments. A process wire module 1200 is passed a component to add statements to the simulation code to affect the wiring of outputs to inputs of the component. Lines 17 and 18 illustrate wire statements of the inputs for the component. In blocks 1201-1203, the module loops selecting each input and generating a wire statement for that input. The component then completes.

Figure 13:
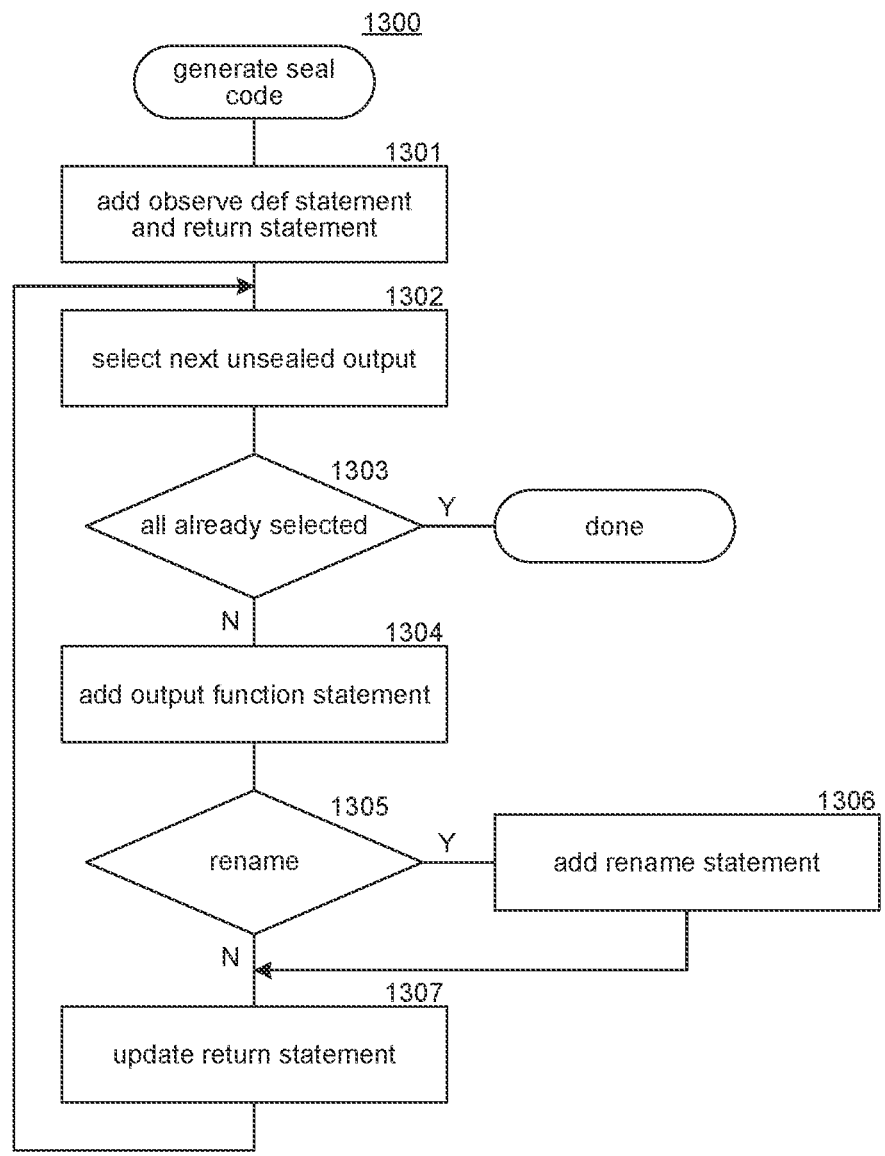
FIG. 13 is a flow diagram that illustrates the processing of a generate seal code module of the CC system in some embodiments.

FIG. 13 is a flow diagram that illustrates the processing of a generate seal code module of the CC system in some embodiments. A generate seal code module 1300 generate code is passed an indication of the unsealed observables designated by a seal statement. In block 1301, the module adds an observe definition statement and a return statement of an observables function to the simulation code. Lines 37 and 44 illustrate such statements. In block 1301, the module selects the next unsealed output designated by the seal statement. In decision block 1303, if all the unsealed outputs have already been selected, then the module completes, else the module continues at block 1304. In block 1304, the module adds a statement that sets the value of the observable. Line 38 illustrates the statement for the observable of the example network. In decision block 1304, if the seal statement indicates to rename the observable, then the module continues at block 1306, else the module continues at block 1307. In block 1306, the module adds a rename statement to the observe function. Line 41 illustrates the statement for renaming the observable. In block 1307, the module updates the return statement to add the observable as the original name or the renamed name and then loops to block 1302 to select the next unsealed output.

Figure 14:
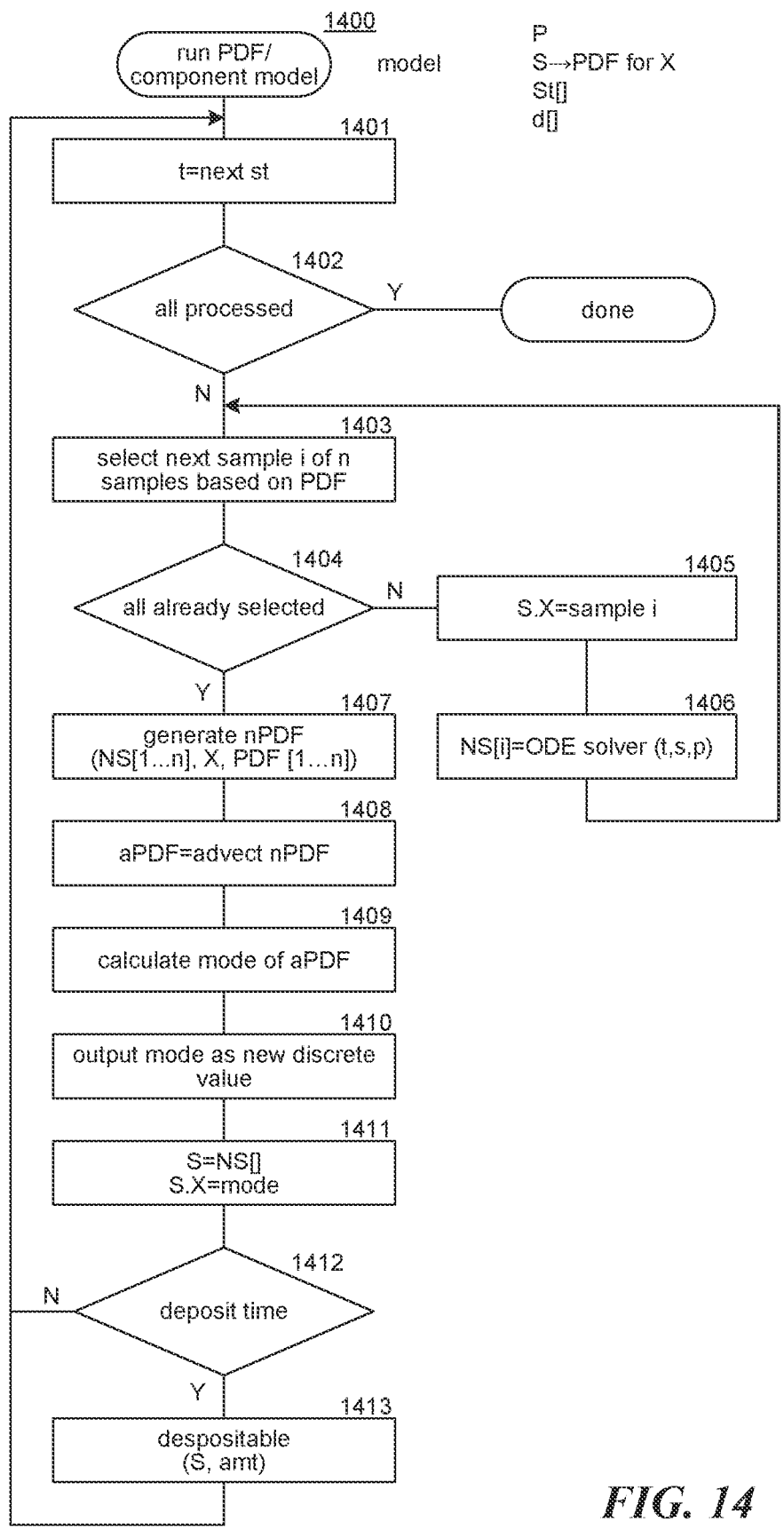
FIG. 14 illustrates a module for modeling a biological system using a PDF with a component-based model that inputs discrete values in some embodiments.

FIG. 14 illustrates a module for modeling a biological system using a PDF with a component-based model that inputs discrete values in some embodiments. A module 1400 is passed parameters p, state s (with a PDF for state x), simulation times st[ ], and depositable times and amounts d [] or a state. The module invokes the ODE solver multiple times for each simulation time and advects the resulting PDF. In block 1401, the modules set time t to the next simulation time. In decision block 1402, if all the simulation times have been processed, then the module completes, else the module continues at block 1403. In blocks 1403-1406, the module loops generating a solution for n sample values i for state x within the range of the PDF and invoking the ODE solver based on that sample value. In block 1403, the module selects a next sample value. In decision block 1404, if n samples have been selected, then the module continues at block 1407, else the module continues at block 1405. In block 1405, the module sets state x to the sample value. In block 1406, the module invokes the ODE solver passing the simulation time state, and parameters and adding the resulting new state to a set of new states ns [] so there is one new state saved for each sample value. The module then loops to block 1403 to select the next sample value. In module 1407, the module generates a new PDF nPDF based on the new states and the probability of each sample value. In block 1408, the module uses the ABM system to advect the new PDF to an advected PDF aPDF. In block 1409, the module calculates a representative value for state x based on the advected PDF such as the mode of the advected PDF. In block 1410, the module outputs an indication of the representative value as the new value of state x. In block 1411, the module sets the state to a one of the new states (e.g., associated with the sample value with the highest probability) and sets state x to the representative value. In decision block 1412, if the next simulation time is a deposit time, then the module continues at block 1413, else the modules loops to block 1401 to set the next simulation time. In block 1413, the module invokes the depositable function generated the CC system and loops to block 1401 to set the next simulation time.

The following paragraphs describe various embodiments of aspects of the ABM system and other systems. An implementation of the systems may employ any combination of the embodiments and aspects of the embodiments. The processing described below may be performed by a computing system with a processor that executes computer-executable instructions stored on a computer-readable storage medium that implements the system.

In some embodiments, a method performed by a computing system for use in determining a characteristic of a state of a system is provided. The method accesses a prior probability density function ("PDF") representing an initial characteristic and parameters of a model of the system. The method accesses a measurement of the state of the system at a measurement time. The method generates an advected prior PDF by advecting a prior PDF to the measurement time by solving an advection equation based on the system model and the prior PDF. The method generates a posterior PDF using a learning technique to learn new values of the parameters based on the advected prior PDF, the system model, the measurement, and a measurement uncertainty. The posterior PDF is for determining the characteristic of the state of the system given the initial characteristic. In some embodiments, the method further comprises determining the characteristic for a later time after the measurement time by advecting the posterior PDF to the later time by solving an advection equation based on the system model and the posterior PDF. In some embodiments, the method further comprises adjusting the posterior PDF to compensate for use of the learning technique wherein the adjusted posterior PDF is used as a next prior PDF when generating a next advected prior PDF. In some embodiments, the determined characteristic is a prediction of state of the system at a future time. In some embodiments, the determined characteristic is an estimate of the characteristic of the state of the system at a past time. In some embodiments, the determining of the characteristic is performed multiple times after the measurement time. In some embodiments, the method further comprises adjusting the posterior PDF to compensate for use of the learning technique wherein the adjusted posterior PDF is used as a next prior PDF when generating a next advected prior PDF. In some embodiments, the method further comprises, for each of a plurality of next measurement times setting a next prior PDF based on a previous posterior PDF of a previous measurement time; accessing a next measurement of the state of the system at the next measurement time; generating an advected prior PDF by advecting the next prior PDF to the next measurement time by solving an advection equation based on the system model and the prior PDF; and generating a posterior PDF using a learning technique to learn new values of the parameters based on the advected prior PDF, the system model, the next measurement, and a measurement uncertainty. In some embodiments, the next prior PDF is set to a previous posterior PDF that has been modified based on uncertainty in the previous posterior PDF. In some embodiments, the learning technique is Bayesian learning. In some embodiments, the system is selected from a group consisting of geological systems, social systems, environmental systems, financial systems, disease progression systems, psychological systems, and biological systems.

In some embodiments, a method performed by a computing system for determining a next characteristic of a state of a system is provided. The method accesses a posterior probability density function ("PDF") generated by advecting a prior PDF to a measurement time to generate an advected prior PDF by solving an advection equation based on a model of the system and learning values for parameters of the model based on the advected prior PDF, the model, a measurement of the system, and a measurement uncertainty. The method generates the next characteristic by advecting the posterior PDF to a next time that is later than the measurement time by solving an advection equation based on the model and the posterior PDF. In some embodiments, the system is a biological system. In some embodiments, the system is selected from a group consisting of geological systems, social systems, environmental systems, financial systems, disease progression systems, psychological systems, and biological systems.

In some embodiments, a computing system for generating a probability density function ("PDF") for determining a characteristic of a state of a system is provided. The computing system comprises one or more computer-readable storage mediums for storing computer-executable instructions and one or more processors for executing the computer-readable instructions stored in the one or more computer-readable storage mediums. The instructions control the computing system to generate an advected prior PDF by advecting a prior PDF to a measurement time of a measurement using a system model of the system, the system model having parameters, the prior PDF representing an initial time. The instructions control the computing system to generate a posterior PDF using a learning technique to learn new values of the parameters based on the advected prior PDF, the system model, and the measurement, wherein the posterior PDF is for determining the characteristic of the state of the system at a later time that is later than the measurement time. In some embodiments, the learning of the new values is further based on a measurement uncertainty. In some embodiments, the computer-executable instructions include instructions to determine the characteristic of the state at the later time by advecting the posterior PDF to the later time by solving an advection equation based on the system model and the posterior PDF. In some embodiments, the computer-executable instructions include instructions to adjust the posterior PDF to compensate for use of the learning technique wherein the adjusted posterior PDF is used as a next prior PDF when generating a next advected prior PDF. In some embodiments, the later time is a future time. In some embodiments, the later time is a past time. In some embodiments, the determining of a determined state is performed for multiple later times after the measurement time. In some embodiments, the computer-executable instructions include instructions to adjust the posterior PDF to compensate for use of the learning technique wherein the adjusted posterior PDF is used as a next prior PDF when generating a next advected prior PDF. In some embodiments, the computer-executable instructions include instructions to, for each of a plurality of next measurement times set a next prior PDF based on a previous posterior PDF of a previous measurement time; access a next measurement of the characteristic of the state of the system at the next measurement time; generate an advected prior PDF by advecting the next prior PDF to the next measurement time by solving an advection equation based on the system model and the prior PDF; and generate a posterior PDF using a learning technique to learn new values of the parameters based on the advected prior PDF, the system model, and the next measurement. In some embodiments, the next prior PDF is set to a previous posterior PDF that has been modified based on uncertainty in the previous posterior PDF. In some embodiments, the learning technique is Bayesian learning. In some embodiments, the system is selected from a group consisting of geological systems, social systems, environmental systems, financial systems, disease progression systems, psychological systems, biological systems, and other systems.

In some embodiments, a method of treating a patient is provided. The method generates a prediction of a characteristic of a state of a biological system of the patient using a probability density function generated based on measurements of the characteristic and a physiological model of the biological system and based on advecting a prior PDF using the measurements and the physiological model. The method infers from the prediction of the characteristic the state of the biological system, the methods a course of treatment for the patient based on the inferred characteristic. The method treats the patient in accordance with the course of treatment.

In some embodiments, the course of treatment is based on a model predictive control system. In some embodiments, the course of treatment relates to dosing of a drug.

In some embodiments, a method of treating a patient is provided. The method generates a prediction of characteristic of a state of a biological system using a probability density function ("PDF") generated based on measurements of the characteristic and a physiological model of the biological system and based on advecting a prior PDF using the measurements and the physiological model. The method determines a course of treatment for the patient based on the prediction of the characteristic. The method treats the patient in accordance with the course of treatment.

In some embodiments, a method performed by one or more computing systems to model behavior of a biological system is provided. The method accesses a cell aging component for modeling dynamics of cell aging of cells of the biological system using a differential equation to model the dynamics of cell aging over time. The cell aging component has a cell age distribution of cells of the biological system, a cell birth rate, a cell reduction rate, and a cell aging rate of the biological system. The differential equation represents effect of the cell birth rate, the cell reduction rate, and the cell aging rate on the cell age distribution. The method accesses a current cell age distribution of the cells of an organ corresponding to a current simulation time. The method receives a current cell birth rate, a current cell reduction rate, and a current cell aging rate corresponding to the current simulation time. The method simulates behavior of the biological system from the current simulation time to a next simulation time to generate a next cell age distribution at the next simulation time by solving the differential equation based on the current cell age distribution, the current cell birth rate, the current cell reduction rate, and the current cell aging rate. In some embodiments, a rate of the cell birth rate, the cell reduction rate, and the cell aging rate is represented as a prior probability density function and the method further repeatedly simulates the behavior of the biological system from the current simulation time to the next simulation time using discrete values sampled from the prior probability density function to generate next cell age distributions. In some embodiments, the method generates a next rate for each sampled rate based on the next cell age distribution for that sample rate and generates a posterior probability density function based on the next rates and the probabilities of the sampled rates indicated by the prior probability density function. In some embodiments, the method advects the posterior probability density function as a next prior probability density function to generate a next posterior probability function. In some embodiments, the differential equation is represented as:

$$u_t + \alpha u_x = \delta_b \partial_x^2 u - \beta u$$

$$(\alpha u - \delta_b u_x)|_{x=0^+} = F_{in}$$

$$(\alpha u - \delta_b u_x)|_{x=1^-} = F_{out}$$

$$u|_{t=t_0} = \psi$$

where $\delta_b$ is a diffusion coefficient, a is an aging rate, $t_0$ is an initial time, $\psi$ is an initial cell age distribution, $\beta$ is an age-independent death rate, $F_{in}$ is total flux at left-boundary (age $x=0^-$), $F_{out}$ is total flux at right-boundary (age $x=1^+$), and u is current cell age distribution.

In some embodiments, a method performed by a computing system generating a model for modeling behavior of a liver of a patient factoring in effect of an administered drug is provided. The method accesses a component library of components. Each component specifies one or more of a parameter, a state, an input, and an output of the component. The components includes a single-species aging component, a pharmacokinetics component, an linear component, and a response curve component. The single-species aging component has component code for modeling behavior of cell aging using a differential equation. The method specifies components to add to the model that include a single-species aging (SA) component, a first and a second pharmacokinetics component (PK1 and PK2), a first and a second response curve component (RE1 and RE2), a first and a second linear component (LC1 and LC2), and a first and second observer component (O1 and O2). The method specifies component code for the PK1, PK2, RE1, RE2, LC1, LC2, O1, and O2 components of the model. The method specifies connections from outputs of components to inputs of the components. The model comprises the combination of the specified components, the component code, and the connections. In some embodiments, the connections are as follows:

| Output | Input |
|---|---|
| PK1 | RE2 |
| RE2 | RC1 |
| RE1:2 and R2 | LC1 |
| O1 and O2 | LC2 |
| LC2 | PK2 |
| LC1 | SA:1 |
| RE1:1 | SA:2 | wherein XX:n represents input or output n for component XX and the O1 and O2 components are sub-components of the SA component. In some embodiments, the component code for the PK1 component inputs a dose of drug and output concentration of the drug in the blood stream of the patient, the RE2 component outputs cell death rate, the RE1 component outputs cell divide rate (RE1:2) and cell birth rate (RE1:1), the LC1 component outputs cell reduction rate, the O1 component outputs number of dead cells, the O2 component outputs number of cells, the LC2 component outputs number of dead cells, and the PK2 component outputs liver enzyme level. In some embodiments, the method compiles the model into implementation code including a function implementing the differential equation. In some embodiments, the method further receives an initial cell age distribution for the SA component and a parameter that specifies cell aging rate and invokes a differential equation solver to solve the differential equation based on a current cell age distribution to generate a new cell age distribution. In some embodiments, the SA component inputs an initial cell age distribution, a cell birth rate, a cell reduction rate, and a cell aging rate. In some embodiments, the specifying of the components and connections is performed using a graphics tool. In some embodiments, the specifying of the components and connections is based on declarative constructs. In some embodiments, the specifying of the components and connections is based on imperative statements.

In some embodiments, a method performed by a computer system for compiling a model of a biological system is provided. The method accesses a definition of the model. The definition specifies components of the model and connections between outputs and inputs of the component. Each component has output component code for calculating output of the component. The components includes a cell aging component for modeling aging of cells of the biological system using a differential equation that is implemented by the differential equation component code of the cell aging component. The method establishes identifiers for parameters, state, inputs, and outputs of the components of the model. The method generates implementation code that includes a differential equation function based on the differential equation component code of the cell aging component. The method generates implementation code that calculates output of the components as specified by the output implementation code. The method generates implementation code that sets inputs of the cell aging component based on outputs of connected components to which the inputs are connected including transitively setting an input of a connected component to the output of a component to which it is connected. In some embodiments, implementation code is in a programming language and the method further compiles the implementation code into executable code. In some embodiments, the method further executes the implementation code to calculate inputs of the cell aging component and invokes a differential equation solver to solve the differential equation as represented by the differential equation code. In some embodiments, the cell aging component having state that includes a current cell age distribution for a current simulation time and the invoked differential equation solver generates a next cell age distribution for a next simulation time.

From the foregoing, it will be appreciated that specific embodiments of the invention have been described herein for purposes of illustration, but that various modifications may be made without deviating from the scope of the invention. For example, the PRP system may be used to predict characteristics for both humans and non-humans. Accordingly, the invention is not limited except as by the appended claims.

We claim:

1. A method performed by a computer system for simulating a biological system, the method comprising:
   accessing a definition of a model of the biological system, the definition specifying components of the model and connections between outputs and inputs of the components, each component having output component code for calculating output of the component, the components including a cell aging component for modeling aging of cells of the biological system using a differential equation that is implemented by a differential equation component code of the cell aging component;
   establishing identifiers for parameters, states, the inputs, and the outputs of the components of the model;
   generating implementation code that:
      includes a differential equation function based on the differential equation component code of the cell aging component;
      calculates outputs of the components as specified by the output component codes of the components; and
      sets inputs of the cell aging component based on outputs of connected components to which the inputs are connected including transitively setting an input of a connected component to the output of a component to which it is connected; and
   simulating, using the implementation code, behavior of the biological system from a current simulation time to a next simulation time, wherein the simulating comprises invoking a differential equation solver to solve the differential equation as represented by the differential equation component code; wherein:
   the cell aging component comprises a state that includes a current cell age distribution for the current simulation time and one or more of a first probability density function (PDF) for a cell birth rate, a second PDF for a cell reduction rate, or a third PDF for a cell aging rate; and
   the invoked differential equation solver generates a next cell age distribution for the next simulation time using one or more values sampled from the one or more of the first PDF for the cell birth rate, the second PDF for the cell reduction rate, or the third PDF for the cell aging rate.

2. The method of claim 1, wherein:
   the implementation code is in a programming language; and
   the simulating further comprises compiling the implementation code into executable code.

3. The method of claim 2, wherein the simulating further comprises executing the executable code to calculate inputs of the cell aging component.

4. A non-transitory computer-readable storage medium including instructions that, when executed by one or more processors of a computing apparatus, cause the computing apparatus to:
   access a definition of a model of a biological system, the definition specifying components of the model and connections between outputs and inputs of the components, each component having output component code for calculating output of the component, the components including a cell aging component for modeling aging of cells of the biological system using a differential equation that is implemented by a differential equation component code of the cell aging component;
   establish identifiers for parameters, states, the inputs, and the outputs of the components of the model;
   generate implementation code that:
      includes a differential equation function based on the differential equation component code of the cell age component;
      calculates outputs of the components as specified by the output component codes of the components; and
      sets inputs of the cell age component based on outputs of connected components to which the inputs are connected including transitively setting an input of a connected component to the output of a component to which it is connected; and
   simulate, using the implementation code, behavior of the biological system from a current simulation time to a next simulation time, wherein the simulating comprises invoking a differential equation solver to solve the differential equation as represented by the differential equation component code; wherein:
   the cell aging component comprises a state that includes a current cell age distribution for the current simulation time and one or more of a first probability density function (PDF) for a cell birth rate, a second PDF for a cell reduction rate, or a third PDF for a cell aging rate; and
   the invoked differential equation solver generates a next cell age distribution for the next simulation time using one or more values sampled from the one or more of the first PDF for the cell birth rate, the second PDF for the cell reduction rate, or the third PDF for the cell aging rate.

5. The non-transitory computer-readable storage medium of claim 4, wherein the implementation code is in a programming language, and wherein the simulating further comprises compiling the implementation code into executable code.

6. The non-transitory computer-readable storage medium of claim 5, wherein
the simulating further comprises executing the executable code to calculate inputs of the cell aging component.

7. A computing apparatus comprising:
one or more processors; and
a memory storing instructions that, when executed by the one or more processors, configure the computing apparatus to:
  access a definition of a model of a biological system, the definition specifying components of the model and connections between outputs and inputs of the components, each component having output component code for calculating output of the component, the components including a cell aging component for modeling aging of cells of the biological system using a differential equation that is implemented by a differential equation component code of the cell aging component;
  establish identifiers for parameters, states, the inputs, and the outputs of the components of the model;
  generate implementation code that:
    includes a differential equation function based on the differential equation component code of the cell age component;
    calculates outputs of the components as specified by the output component codes of the components; and
    sets inputs of the cell age component based on outputs of connected components to which the inputs are connected including transitively setting an input of a connected component to the output of a component to which it is connected; and
  simulate, using the implementation code, behavior of the biological system from a current simulation time to a next simulation time, wherein the simulating comprises invoking a differential equation solver to solve the differential equation as represented by the differential equation component code; wherein:
    the cell age component comprises a state that includes a current cell age distribution for the current simulation time and one or more of a first probability density function (PDF) for a cell birth rate, a second PDF for a cell reduction rate, or a third PDF for a cell aging rate; and
    the invoked differential equation solver generates a next cell age distribution for the next simulation time using one or more values sampled from the one or more of the first PDF for the cell birth rate, the second PDF for the cell reduction rate, or the third PDF for the cell age rate.

8. The computing apparatus of claim 7, wherein the implementation code is in a programming language, and wherein the simulating further comprises compiling the implementation code into executable code.

9. The computing apparatus of claim 7, wherein the simulating further comprises executing the executable code to calculate inputs of the cell aging component.

* * * * *